United States Patent
Spears et al.

(10) Patent No.: US 9,149,223 B2
(45) Date of Patent: Oct. 6, 2015

(54) METHOD AND APPARATUS FOR MEASURING EXPENDED ENERGY

(75) Inventors: Iain R. Spears, Middlesbrough (GB); Pierre Lagadec, Middlesbrough (GB); Simon W. Bateson, Yarm (GB); Simon Read, Sheffield (GB)

(73) Assignee: Teesside University, Middlesbrough (GB)

( * ) Notice: Subject to any disclaimer, the term of this patent is extended or adjusted under 35 U.S.C. 154(b) by 0 days.

(21) Appl. No.: 14/125,972

(22) PCT Filed: Jun. 18, 2012

(86) PCT No.: PCT/GB2012/051396
§ 371 (c)(1),
(2), (4) Date: Dec. 13, 2013

(87) PCT Pub. No.: WO2012/172375
PCT Pub. Date: Dec. 20, 2012

(65) Prior Publication Data
US 2014/0142864 A1   May 22, 2014

(30) Foreign Application Priority Data

Jun. 16, 2011 (GB) .................................. 1110217.5

(51) Int. Cl.
*G01D 1/00* (2006.01)
*A61B 5/22* (2006.01)
(Continued)

(52) U.S. Cl.
CPC ................. *A61B 5/22* (2013.01); *A61B 5/1118* (2013.01); *A61B 5/221* (2013.01); *A61B 5/4866* (2013.01);
(Continued)

(58) Field of Classification Search
CPC .. A63B 24/0062; A61B 5/1118; A61B 5/221; A61B 5/4866; A61B 5/6895; A61B 5/22
USPC ........................................................ 702/127
See application file for complete search history.

(56) References Cited

U.S. PATENT DOCUMENTS 8,075,462 B1 * 12/2011 Hinds et al. .................... 482/125
8,626,472 B2 * 1/2014 Solinsky ........................ 702/160
(Continued)

FOREIGN PATENT DOCUMENTS

EP           1836959 A1    9/2007
WO    WO 2008/132105 A1   11/2008

OTHER PUBLICATIONS

International Search Report and Written Opinion for PCT/GB2012/051396 dated Oct. 5, 2012 (10 pages).
(Continued)

*Primary Examiner* — Tung S Lau
*Assistant Examiner* — Xiuquin Sun
(74) *Attorney, Agent, or Firm* — Taft Stettinius & Hollister, LLP; Ryan O. White

(57) ABSTRACT

A method of measuring expended energy of a moving body, including providing a first sensor for measuring data of a first part of the moving body; providing a second sensor for measuring data of a second part of the moving body, wherein the second part is moveable relative to the first part and connected to the first part by a first resistive deformable element that is external to the moving body; using the first sensor to make a first measurement and subsequently calculating a global expended energy of the first part relative to a reference frame; using the second sensor to make a second measurement and subsequently calculating a relative expended energy of the second part relative to the first part; and calculating the total expended energy of the moving body by summing the global expended energy with the relative expended energy.

24 Claims, 12 Drawing Sheets

(51) Int. Cl.
*A61B 5/00* (2006.01)
*A61B 5/11* (2006.01)
*A63B 21/055* (2006.01)
*A63B 21/00* (2006.01)
*A63B 71/06* (2006.01)
*A63B 21/04* (2006.01)
*A63B 23/035* (2006.01)
*A63B 23/12* (2006.01)
*A63B 24/00* (2006.01)

(52) U.S. Cl.
CPC ........... *A61B 5/6895* (2013.01); *A63B 24/0062* (2013.01); *A61B 5/1112* (2013.01); *A61B 5/1114* (2013.01); *A63B 21/0442* (2013.01); *A63B 21/0552* (2013.01); *A63B 21/0557* (2013.01); *A63B 21/1419* (2013.01); *A63B 21/1469* (2013.01); *A63B 23/03541* (2013.01); *A63B 23/1209* (2013.01); *A63B 71/0622* (2013.01); *A63B 2024/0096* (2013.01); *A63B 2220/12* (2013.01); *A63B 2220/13* (2013.01); *A63B 2220/16* (2013.01); *A63B 2220/40* (2013.01); *A63B 2220/806* (2013.01); *A63B 2225/20* (2013.01); *A63B 2225/50* (2013.01); *A63B 2230/75* (2013.01)

(56) References Cited

U.S. PATENT DOCUMENTS

2004/0176226 A1*  9/2004  Carlson .......................... 482/112
2005/0033200 A1    2/2005  Soehren et al.

OTHER PUBLICATIONS

Andre, et al: "Recent Advances in Free-Living Physical Activity Monitoring: A Review", Journal of Diabetes Science and Technology, vol. 1, No. 5, pp. 760-767 (Sep. 15, 2007).
International Preliminary Report on Patentability for PCT/GB2012/051396 dated Dec. 17, 2013 (6 pages).

* cited by examiner

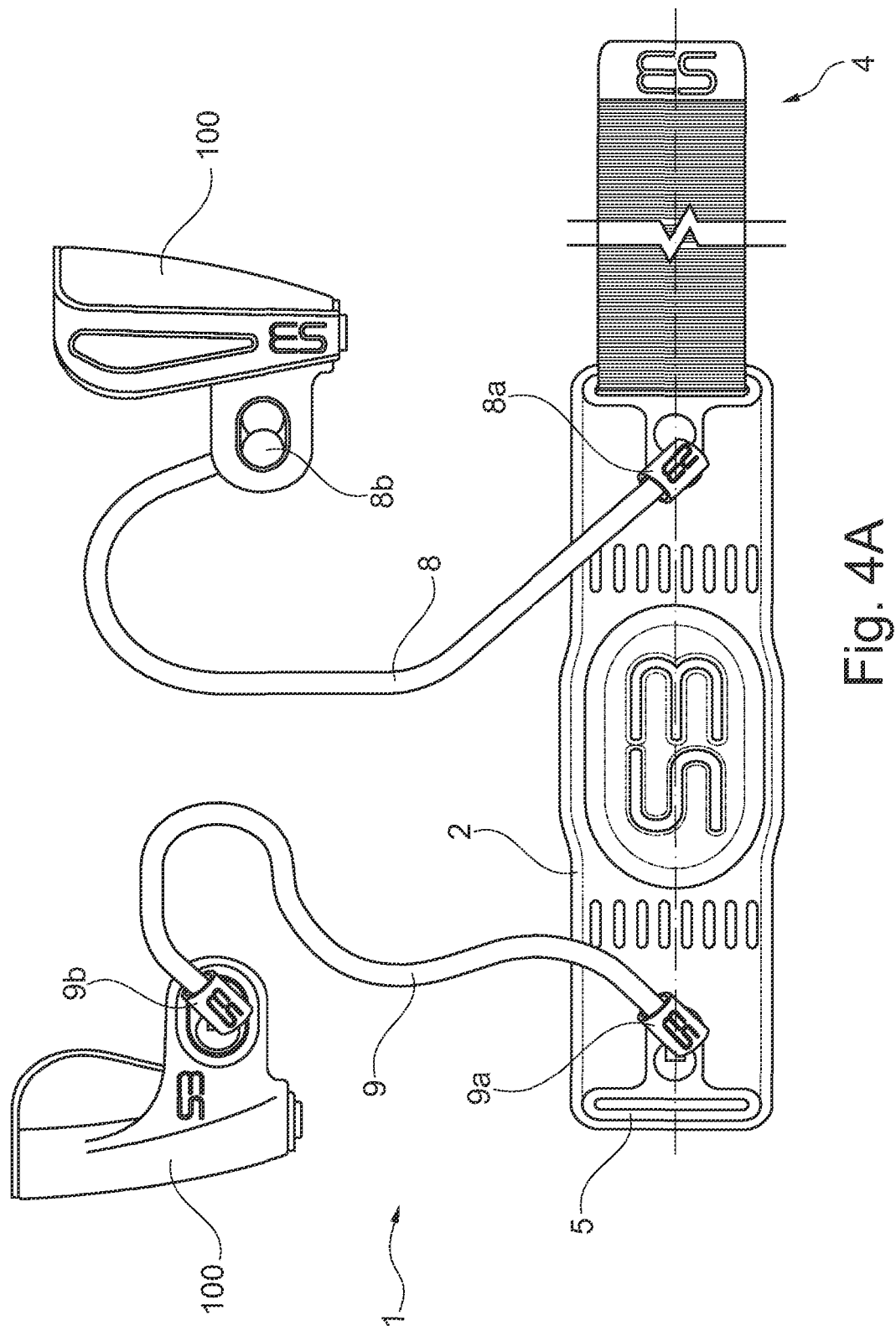

METHOD AND APPARATUS FOR MEASURING EXPENDED ENERGY

This application is a U.S. national stage application under 35 U.S.C. §371 of PCT International Application Serial No. PCT/GB2012/051396, which has an international filing date of Jun. 18, 2012, designates the United States of America, and claims the benefit of GB Application No. 1110217.5, which was filed on Jun. 16, 2011. The disclosures of each of these prior applications are hereby expressly incorporated by reference in their entirety.

This invention relates to a method and apparatus for measuring expended energy, and in particular to a method and apparatus for measuring total expended energy by measuring external work done and internal work done of a moving body, such as an exercising person.

BACKGROUND

Type 2 diabetes mellitus (T2D) is characterised by insulin resistance which may be combined with relatively reduced insulin secretion. In the early stage of T2D, the predominant abnormality is reduced insulin sensitivity. The risk of developing T2D is largely due to lifestyle factors most notably lack of physical activity and poor diet.

Insulin resistance is characterised by an abnormal regulation of blood glucose concentration leading to excess amounts of glucose circulating the body and a failure of biochemical reactions at the skeletal muscle to utilise the energy source. The role of insulin in stimulating the transport of glucose across the muscle cell membrane via activation of the glucose transporter 4 (GLUT4) is crucial for allowing glucose uptake, however, in diabetic patients, failure to produce insulin in the pancreas leads to diminished amounts of insulin transported into the blood stream (Turcotte & Fisher, 2008). As skeletal muscle is the most responsive to insulin and the main source of blood glucose clearing, it is essential that skeletal muscle is stimulated in the most efficient way to 'dispose' of the excess glucose in the blood by physical exercise.

The onset of exercise increases glucose transport at working muscles by stimulating GLUT4 from within the muscle cell to the surface of the cell which causes a number of metabolic changes, the most important being increased glucose uptake (Lund et al., 1995). During the onset of exercise, intra-muscular, readily available stores of energy (glycogen) are utilised as the primary source for muscle contraction, this leads to the recruitment of the Krebs cycle to, in basic terms, recycle energy by additional glucose and sustained oxygen consumption (aerobic glycolysis), however, anaerobic exercise relies heavily on increased stores on muscle glycogen as a result of training and replenishes stores post exercise as stimulation of muscle glucose uptake persists for an extended period of time post-exercise. Glycogen repletion is characterised by a marked and persistent increase in insulin action (Richter, 1996). Based on this premise, it is important to understand which exercise parameters (intensity, duration, frequency and mode) and the characteristics of the individual (presence of disease, fitness and genetic pre-dispositions) are most beneficial to maximising adaptations to the cells involved with muscle glucose clearing (Sigal et al., 2004), especially in diabetic patients.

There is evidence to suggest that endurance and resistance exercise training lead to adaptations specific to that training regime. Endurance exercise training allows skeletal muscle to utilise O2 and blood-borne fuels, whereas resistance training leads to improvements in force generation (muscle hypertrophy and contractile properties). Both training approaches lead to increased muscle GLUT4 which probably contributes to the increased capacity for insulin-stimulated glucose transport in trained subjects which has implications for insulin-resistant patients (Sigal et al., 2004). Furthermore, both training mechanisms are similar with relation to increased glucose disposal, however, resistance training has the advantage by increasing muscle mass (and therefore glucose storage space) (Holten et al., 2004; Ivy, 2002), but also increase mitochondrial function and density which has been found in elderly subjects or potentially diabetes sufferers (Jubrais et al., 2001). Emerging data on the outcome of different resistance training protocols can conflict, a single session reduced glucose infusion rate during an insulin clamp, however no decrease or increase occurred when 3 sessions were performed (Howlett et al., 2007). Conversely, 1 session (3 sets, 8-12 reps during 8 exercises) decreased the glucose area under the curve during an oral glucose tolerance test by ~12% compared to pre-exercise levels, 24 hours after exercise in T2D women (Fenicchia et al., 2004).

Other studies have shown a 15% increase compared to control group following 3 sets×10 rep.max in upper and lower body exercise during oral glucose tolerance test (6 hours post exercise (Venables et al., 2007). Another resistance training protocol yielded similar results (13% higher glucose absorption) following 8×10 reps at 75% of 1 rep.max after an insulin injection given 24 hours post exercise (Koopman et al., 2005). Results from a study by Babraj et al, (2009) found that following a 2 week high intensity training program of cycle sprint training against 7.5% body weight reduced the area under the plasma glucose by 12%. A similar protocol to Babraj found that sprint interval training (against 7.5% body weight) increased muscle glycogen content by ~50% which suggests this form of exercise is capable of inducing post-exercise glucose absorption in diabetic patients.

The American College of Sports Medicine (ACSM) recommends a resistance training regime for T2D individuals whenever possible including 8-10 exercises involving major muscle groups with a minimum of 1 set of 10-15 reps to near fatigue. This regime can be altered to increase the number of sets or the intensity of exercise in certain individuals, this data was published prior to studies by Dunstand et al (2002) and Castaneda et al (2002) who found significant results following 3 sets of 8-10 repetitions of >85% 1 rep.max which should be advocated into further studies. Although 1 set may increase muscular strength, it appears that three or more sets of resistance training may produce greater metabolic benefit in type 2 diabetic patients (Sigal et al., 2004).

An area for consideration with regards to resistance training is the type of muscular action performed as evidence has shown that eccentric muscle contractions (muscle lengthening, e.g. elbow extension against a resistance) may actually damage the muscle and inhibit a metabolic adaptation. For instance, 30 mins of down-hill running caused a 36% decline in insulin-stimulated glucose disposal 48 hours after exercise (Kirwan et al., 1992). Likewise 2 days following intense one-legged eccentric exercise (4 sets knee extension/flexion, 5 mins per set using an isokinetic dynamometer) resulted in a decline in muscle GLUT 4 content and 15% decrease in glucose infusion rate during an insulin clamp (Asp et al., 1996).

Implications for high resistance exercise using weights may be acceptable for young individuals or those with long-standing diabetes. Moderate weight training programs that utilize light weights and high repetitions can be used for maintaining or enhancing upper body strength in nearly all patients with diabetes (Turcotte & Fisher, 2008). Current recommendations for improving glycemic control involve performing moderate to vigorous intensity aerobic and resistance exercise for several hours per week (American Diabetes Association, 2008; Lakka et al., 2007). However, the general population fails to follow such regimes due to lack of time, motivation and adherence (Godin et al., 1994), therefore resistance training in a manageable form (such as exergaming) may provide beneficial adaptations which are more appealing to wider public population.

As discussed above, it is accepted that exercise reduces the risk of developing T2D. Indeed, the promotion of exercise is a cost-effective strategy of reducing the risk of people developing T2D in a population. It is also recognised that achieving a healthy balance between energy input and energy expenditure is an important factor in reducing the risk of developing T2D. There has been much work on developing methods of measuring energy expenditure which have been important in helping the understanding of the relationship between physical activity and health. It is recognised that regular and accurate self-monitoring of energy expenditure in the free-living environment can provide important feedback to a patient, thereby increasing self-awareness which is the prerequisite for healthy decision making and long-term lifestyle change.

The, location and type of muscle loading and intensity and duration are all important parameters in the prevention of T2D. At present, there are several known ways of measuring energy expenditure but these are generally focussed on the calorific energy intensity (termed EE) of the whole body. While such data is vital in terms of measuring calories burned, levels of exercise intensity and duration during free-living, the prior art systems are not configured to give specific energy-related information corresponding to the movement of specific, individual parts of the body. Simply taking a systemic measure of overall calories used will generally not be sufficient to quantify the potential benefits of exercise, and will therefore not be sufficient to maximise the potential benefits of future exercise interventions.

The number of calories a person burns is an important and actionable parameter for many applications and disease conditions. These include metabolic disorders, weight control (loss, gain, or maintenance), sports performance, and body composition changes. True total energy expenditure (TEE) is a much more useful parameter but is very difficult to measure, and all known techniques make use of approximations of one kind or another, and/or are impractical due to the nature of data collection. An overview of the techniques for measuring energy expenditure can be found in Andre at al., 2007. Known techniques include indirect calorimetry, the use of doubly labelled water, or the use of heart rate monitors, pedometers, global positioning system (GPS) monitors, accelerometers, multisensor devices or multilocation devices. Each of these prior art systems and methods are described below.

Indirect Calorimetry

Indirect calorimetry measures the oxygen and carbon dioxide that a person inhales and exhales and indirectly determines the calories burned during a given period. This method is undertaken in laboratory conditions using a metabolic cart and is widely regarded in the research community as a standard measurement method, presently. However, most metabolic carts for indirect calorimetry measurements are large and bulky and are not suited for monitoring outside the laboratory setting. In addition, the required devices are expensive, costing in the region of $20,000 for a basic system, although more portable, less costly metabolic carts have now become available. Typically, however, portable systems have higher error rates compared with their larger stationary counterparts. Both stationary and portable metabolic carts require the user to breathe through a mouthpiece or mask and are usually used in a laboratory.

Doubly Labelled Water (DLW)

The DLW stable isotope method is based on the principle that in a loading dose of $^{2}H_{2}^{18}O$ given to a subject, $^{18}O$ is eliminated from the body as $CO_2$ and water, while deuterium is eliminated from the body as water. The rate of $CO_2$ production, and, thus, energy expenditure, is calculated from the difference of the two elimination rates. The subjects give urine and saliva specimens before and after drinking an initial dose of DLW and then give a final urine specimen 1 to 2 weeks later. During the period between initial and final samplings, subjects are free to carry out their normal activities. This is a safe procedure, as the isotopes are stable and emit no radiation. Limitations of the DLW method include a high cost (~$1500/person), the need for specialized equipment and expertise to implement the techniques. Additionally, the method can only be used to measure expenditure over a long period of time (e.g., 10-14 days). DLW has an error rate of about 5% over a 2-week period because of starting and ending conditions.

Heart Rate Monitors

Heart rate (HR) is one of the fundamental vital signs and is related to the level of physical exertion. A person's HR increases linearly with oxygen consumption, especially for moderate to strenuous activity. HR monitoring is quite common and is often used as part of an exercise prescription. Furthermore, most HR monitor companies have released software for converting HR data into an estimate of energy expenditure (e.g., Polar, Kempele, Finland). Several studies have found that calibration is required to create a curve between the subject's HR and estimated energy expenditure, involving a submaximal stress test at moderate activity levels. Additionally, HR monitors are typically only accurate for moderate to vigorous activities, as in lower-intensity activities. Confounds such as stress, emotions, caffeine intake, ambient temperature, or illness may have a significant impact on a person's HR and may therefore skew results.

Chest-strap HR monitors can be a burden to participants because of the constriction required across the chest to maintain good skin contact. Electrode-based HR monitors are difficult to wear, as placement, skin treatment, and irritation can be significant issues and detriments to long-term wear. Subjects have shown poor compliance at wearing heart rate monitors in free-living trials. Additionally, many HR monitors receive interference from electrical equipment. Thus, signal transmission is prone to interference.

Pedometers

Pedometers, by definition, measure footfalls. The advantage of pedometers is their low cost, ranging from $15 to $300, and wide availability. In general, pedometers are not accurate when used for activities that do not involve footfalls (e.g., weight lifting, biking, household activities). Even for ambulatory activities, pedometers have been found to be inaccurate at both counting steps and assessing distance walked.

In most cases, pedometers (at the higher end) can be accurate at counting steps, although they are much less accurate at predicting energy expenditure, even during walking, with error rates of ±30%. Whilst a pedometer can be used as a coaching or self-monitoring tool to help people set goals and increase their physical activity levels, they do not measure the intensity, duration, or frequency of physical activity.

Global Positioning System (GPS) Monitors

Several devices based on GPS are known that compute speed and distance traveled and, from that information, estimate calories expended for a particular activity (e.g., walking/ running, road biking). The accuracy of these products is only beginning to be assessed adequately. Even for outdoor activity, where the GPS signal is strongest, some research indicates that these products may overestimate energy expenditure except for fast walking. Although GPS receivers have become quite wearable for short durations, long-term wear may be uncomfortable. Furthermore, because the monitors only work outdoors and for activities involving true translational motion, these devices have significant limitations with respect to being a suitable free-living monitor of energy expenditure. Most currently available devices either report their results on the device itself or to a personal computer.

Multisensor Devices

Most of the single-sensor based systems that are appropriate for free-living activities involve surrogates for energy expenditure, e.g. measuring steps, motion, heart rate, location on the planet, or expired oxygen. All of these quantities provide indirect measures of energy expenditure.

Low motion might indicate rest or it might indicate physical activity using a part of the body far from the accelerometer. Moderate motion might indicate physical activity or it might indicate riding in a moving vehicle on a rough road. By adding another variable, such as heart rate, these different contexts can be disambiguated. For example, riding in a car will typically induce lower heart rates than moderate physical activity, and subjects at rest will typically have lower heart rates than those performing low-motion physical activity. By taking advantage of the science of data fusion, multisensor systems typically achieve higher accuracies than single sensor systems while typically keeping overall costs moderate.

Like single sensor devices, multisensor devices require sensors in skin contact which may be inconvenient or impractical for the type of activity being monitored.

Another multisensor system is the Garmin® Forerunner, which utilizes GPS, heart rate, and optional foot pod and biking cadence/speed sensors to provide "fill in" data if the GPS signal drops out.

A further multisensor monitor is the SenseWear® Pro3 (BodyMedia Inc., Pittsburgh, Pa.). The SenseWear® armband (SWA) is a small, wireless, and wearable body monitor worn on the back of the upper right arm. The SWA utilizes a combination of sensors. A proprietary heat-flux sensor measures the amount of heat being dissipated by the body by measuring the heat loss along a thermally conductive path between the skin and a vent on the side of the armband. Skin temperature and near-armband temperature are also measured by sensitive thermistors. The armband also measures galvanic skin response (the conductivity of the wearer's skin), which varies as a consequence of physical and emotional stimuli. A two-axis accelerometer tracks the movement of the upper arm and provides information about body position. Additionally, a wireless display device is available that can be worn as a watch or clipped to clothing that displays the calories burned, steps taken, and minutes spent in moderate and vigorous physical activity for today, yesterday, and from the time a trip button was pressed.

The SWA utilizes pattern detection algorithms that utilize the physiologic signals from all the sensors to first detect the wearer's context and then apply an appropriate formula to estimate energy expenditure from the sensor values. The armband can recognize many basic activities, such as weight lifting, walking, running, biking, resting, and riding in a car, bus, or train. Other activities are classified into combinations of these basic activities; for example, baseball could be broken down into a combination of mostly near-restful activity and running. The armband can be worn comfortably during a person's normal life and does not require any time in the laboratory for uncomfortable measurements. Laboratory tests indicate that the device is accurate across a broad range of activities and performs well when compared to DLW in diabetic and obese subjects with only an 8% average error.

Accelerometers

Accelerometers operate by measuring acceleration along a given axis, using any of a number of technologies, including piezoelectric, micromechanical springs, and changes in capacitance. Often, multiple axis measurements are bundled into a single package, allowing two and three axis accelerometers. The major function of accelerometers is that the sensor converts movements into electrical signals that are proportional to the muscular force producing motion. Most accelerometers compute energy expenditure by first rectifying the accelerometer signal and then integrating to compute accelerometer counts. Typically, these counts are then multiplied by a constant and added to a separate constant to compute energy expenditure.

Moreover, accelerometer equations have been developed for specific activities (e.g., walking and running, sometimes rest) and do not estimate other activities accurately (e.g., stationary biking, elliptical trainer). Additionally, accelerometers are subject to motion artifacts from activities such as driving in a car or riding on a train. The consensus appears to be that for activities composed entirely of flat-ground ambulation and rest, accelerometers can provide objective measures of activity. Advantages of these types of activity monitors are that they are low to moderate in cost ($50 to more than $1000) and are typically relatively easy to use. Because of the complex nature of some of these devices, as well as the size, subject compliance can sometimes become an issue.

More complex equations for estimating energy expenditure from counts are being developed in this technological area. In these methods, the coefficient of variation of the accelerometry signal is utilized to select an appropriate regression equation. This works because the coefficient of variation of regular walking activity is lower than for free-living activities such as house cleaning. Essentially, this idea utilizes two aspects of a signal: first to classify and then to predict.

Additionally, it is known that the indirect process of determining position from accelerometry data (and accelerometer-based systems [e.g. inclinometers]) is problematic. Errors rapidly accumulate during the integration process and additional information (such as initial conditions) are required for determination of integration constants. Consequently, attempts to track motion by integration of even the most accurate accelerometer signals have been unsuccessful unless low-pass filtering is permitted at each integration or very high quality, expensive and bulky equipment is used. For the purposes of exergaming where an unknown range of non-cyclical movements will occur and the gamer must be free to move unrestricted, neither approach is feasible.

Multilocation Devices

Given that some of the problems of predicting energy expenditure from motion come from an activity that utilizes a part of the body not being measured (e.g., stationary biking), one solution is to utilize accelerometers on multiple parts of the body. Two devices, the DynaPort (McRoberts, B V, The Hague, The Netherlands) and the IDEEA monitor (MiniSun, Fresno, Calif.), utilize this technique. The IDEEA monitor classifies more than 30 activities, with high reported accuracy, and utilizes five accelerometers attached via medical tape to the chest, the underside of each foot, and the front of each thigh. Wires connect the accelerometers to a belt-worn recorder. The accuracy of the device appears to be good, as they are reported to be accurate to within 10% for energy expenditure for some activities. In general, these devices tend to be expensive (more than $1000) and have a significant ease-of-use problem. Many single-location devices are seen as unattractive and inconvenient by the user, especially those that require taping multiple electrodes to locations only accessible when the user is disrobed.

An example of a known system for monitoring the exertion of a user is described in U.S. Pat. No. 5,524,637, which comprises one or more sensors attached to a user for measuring the user's motion. An algorithm is used to determine what kind of activity the user is doing, and at what level of intensity, based on the sensor measurements. A level of overall exertion (e.g. number of calories burned) is then estimated from a look-up table, matrix, formula, or decision flowchart based on the determined type and level of exercise.

It is an object of the present invention to provide an alternative method and apparatus for measuring the total expended energy of a moving body that, in at least one embodiment, improves over the prior art.

BRIEF SUMMARY OF THE DISCLOSURE

In accordance with a first aspect of the present invention there is provided a method of measuring expended energy of a moving body, comprising the steps:
  i) providing at least one first sensor for measuring position data and/or orientation data and/or dynamic data of a first part of the moving body;
  ii) providing at least one second sensor for measuring relative position data and/or orientation data and/or dynamic data of a second part of the moving body, wherein the second part is moveable relative to the first part and connected to the first part by a first resistive deformable element;
  iii) using the at least one first sensor to make a first measurement of the position and/or orientation and/or dynamics of the first part over a period of time and subsequently calculating a global expended energy of the first part relative to a reference frame from the first measurement;
  iv) using the at least one second sensor to make a second measurement of the position and/or orientation and/or dynamics of the second part over said period of time and subsequently calculating a relative expended energy of the second part relative to the first part from the first and second measurements, wherein the calculation includes the energy required to deform the first resistive deformable elements when moving the second part relative to the first part; and
  v) calculating the total expended energy of the moving body by summing the global expended energy with the relative expended energy;
    wherein the at least one first sensor comprises a global positioning system (GPS) sensor and/or an inertial measurement unit and/or a first plurality of reference indicia measurable by an image capture device; and
  the at least one second sensor comprises an inertial measurement unit and/or a second plurality of reference indicia measurable by an image capture device.

Thus the method provides a convenient and accurate method of measuring total expended energy of a moving body that is particularly suited to monitoring a moving human during exercise. The method according to the first aspect of the present invention may be performed outside of a lab for a relatively low cost in comparison to prior art methods. The resistive deformable bands add an additional resistive force which increases the energy required to move the second part relative to the first, thereby making exercise more effective. The additional energy required is factored into the total calculation of energy expenditure.

In a preferable embodiment, the method further comprises the steps:
  vi) providing at least one nth sensor for measuring relative position data and/or orientation data and/or dynamic data of an nth part of the moving body, wherein the nth part is moveable relative to an ith part, where n>2 and i<n;
  vii) using the at least one nth sensor to make an nth measurement of the position and/or orientation and/or dynamics of the nth part over said period of time and subsequently calculating a relative expended energy of the nth part relative to the ith part from the ith and nth measurements; and
  wherein the step of calculating the total expended energy of the moving body comprises summing the global expended energy with all calculated relative expended energies for each nth and ith part.

Thus the moving body can be treated as a large kinetic chain comprising many parts, and the method may be used to calculated the total expended energy of the whole moving body.

In a preferable embodiment, the nth part is connected to an ith part by an nth resistive deformable element. Thus, some or all of the moveable parts of the moving body may experience additional resistance to movement thereby requiring more energy to move. All the additional energy required to deform the resistive deformable elements is included in the calculation of total expended energy, Preferably, each at least one second sensor, and any nth sensor present, is arranged to produce a three-dimensional rotation matrix for each of the second and any nth part. Further preferably, each three-dimensional rotation matrix is updated by the respective sensor periodically. Each three-dimensional rotation matrix is preferably updated by the respective sensor 100 times per second.

In one preferable embodiment, the at least one first sensor is positioned close to the centre of mass of the moving body.

Preferably the moving body is a moving human body, and further preferably, the step of calculating relative expended energy of the second part relative to the first part and/or any nth part relative to any ith part, if present, includes using inertial characteristic data associated with the second and any ith part, where the inertial characteristic data includes the relative masses of the body parts and/or the mass moments of inertia of each body part. In a particularly preferable embodiment, the inertial characteristic data is obtained, at least partly, from a data table.

In a further preferable embodiment, the method further comprises the step of running a forward dynamics simulation of the moving body to produce a second calculation of total expended energy, and iteratively improving the simulation using the first calculation of expended energy.

In any embodiment, the calculated global or relative energy is preferably derived from the integral of a power-time measurement obtained from said first, second and any nth measurement.

In a particularly preferable embodiment, the first resistive deformable element and any nth resistive deformable element is an elasticated band.

In accordance with a second aspect of the present invention, there is provided an apparatus for measuring expended energy of a moving body, comprising:

at least one first sensor for measuring position data and/or orientation data and/or dynamic data of a first part of the moving body;

at least one second sensor for measuring relative position data and/or orientation data and/or dynamic data of a second part of the moving body, wherein the second part is moveable relative to the first part; and a first resistive deformable element for connecting the second part to the first part, wherein the first resistive deformable element is arranged to deform and act to resist deformation when the second part is moved relative to the first part;

a control unit communicably coupled to the at least one first and second sensors to receive measurement data therefrom;

wherein the at least one first sensor is arranged to make a first measurement of the position and/or orientation and/or dynamics of the first part over a period of time and transmit the first measurement data to the control unit;

the at least one second sensor is arranged to make a second measurement of the position and/or orientation and/or dynamics of the second part over said period of time and transmit the second measurement data to the control unit; and the control unit is arranged to calculate a global expended energy of the first part relative to a reference frame from the first measurement, calculate a relative expended energy of the second part relative to the first part from the first and second measurements, wherein the calculation of relative expended energy includes the energy required to deform the first resistive expended energy includes the energy required to deform the first resistive deformable element when moving the second part relative to the first part, and calculate the total expended energy of the moving body by summing the global expended energy with the relative expended energy;

wherein the at least one first sensor comprises a global positioning system (GPS) sensor and/or an inertial measurement unit and/or a first plurality of reference indicia measurable by an image capture device; and the at least one second sensor comprises an inertial measurement unit and/or a second plurality of reference indicia measurable by an image capture device.

Preferably, the apparatus further comprises an nth resistive deformable element for connecting the nth part to an ith part, wherein the nth resistive deformable element is arranged to deform and act to resist deformation when the nth part is moved relative to the ith part.

Preferably, the apparatus further comprises at least one nth sensor communicably coupled to the control unit for measuring relative position data and/or orientation data and/or dynamic data of an nth part of the moving body, wherein the nth part is moveable relative to an ith part, where n>2 and i<n;

wherein the at least one nth sensor is arranged to make an nth measurement of the position and/or orientation and/or dynamics of the nth part over said period of time and transmit the nth measurement to the control unit subsequently calculating a relative expended energy of the nth part relative to the ith part from the ith and nth measurements; and wherein the step of calculating the total expended energy of the moving body comprises summing the global expended energy with all calculated relative expended energies for each nth and ith part.

Further preferably, the sensors are arranged on, or form part of, an item of clothing, and the moving body comprises the wearer of the item of clothing. The sensors are preferably arranged on the item of clothing such that, when worn, the at least one first sensor is arranged to measure position data and/or orientation data and/or dynamic data of the Lumber vertebrae of the wearer, and the at least one second sensor is arranged to measure position data and/or orientation data and/or dynamic data of the Thoracic vertebrae of the wearer.

Each sensor is preferably connected to at least one other sensor by a cable, wherein the cable is arranged to carry electrical power to the sensors and/or allow the transfer of data between the sensors.

Preferably, the apparatus further comprises a transmitter communicably coupled to the sensors, wherein measurement data is transmittable to the control unit via the transmitter.

In a particularly preferable embodiment, the apparatus according to the second aspect of the present invention is used to perform the method according to the first aspect of the present invention.

In accordance with a third aspect of the present invention, there is provided an exercise system comprising:

an apparatus according to the second aspect of the present invention;

a computer system loaded with a game and in communication with the apparatus; and a display unit communicably coupled to the computer system for displaying the game;

wherein the measurements made by the sensors are used by the computer to control the game, and the calculated total expended energy of the moving body is used as part of the game.

Preferably, the game comprises several stages that are completed upon the total expended energy exceeding a predetermined threshold.

In one aspect of the present invention, there is provided a method of measuring expended energy of a moving body (and associated apparatus for performing the method), comprising the steps:

(i) disposing at least one first sensor on or adjacent a first part of a moving body for measuring position data and/or orientation data and/or dynamic data thereof;

(ii) disposing at least one second sensor in a handgrip device held by hand of the moving body for measuring relative position data and/or orientation data and/or dynamic data thereof, wherein the handgrip is moveable relative to the first part and connected thereto by a first resistive deformable element;

(iii) using the at least one first sensor to make a first measurement of the position and/or orientation and/or dynamics of the first part over a period of time and subsequently calculating a global expended energy of the first part relative to a reference frame from the first measurement;

(iv) using the at least one second sensor to make a second measurement of the position and/or orientation and/or dynamics of the hand over said period of time and subsequently calculating a relative expended energy of the hand relative to the first part from the first and second measurements, wherein the calculation includes the energy required to deform the first resistive deformable element when moving the hand relative to the first part; and (v) calculating the total expended energy of the moving body by summing the global expended energy with the relative expended energy;

wherein the at least one first sensor comprises a global positioning system (GPS) sensor and/or an inertial measurement unit and/or a first plurality of reference indicia measurable by an image capture device; and the at least one second sensor comprises an inertial measurement unit and/or a second plurality of reference indicia measurable by an image capture device.

Further aspects of the present invention are defined in the appended claims.

BRIEF DESCRIPTION OF THE DRAWINGS

Embodiments of the invention are further described hereinafter with reference to the accompanying drawings, in which:

FIG. 4A shows an apparatus including a belt and handpieces connected to the belt by resistive deformable elements for use with the present invention;

DETAILED DESCRIPTION

The present invention seeks to provide a method and apparatus for calculating the total energy expenditure of a moving body, such as the human body. In particular, the present invention models the moving body as a kinetic chain of connected segments that are movable relative to one another. The mechanical work of such a movable body is equal to the summation of the internal and external work done. The latter is dependent on the movement of the centre of mass (COM) relative to the environment (i.e. a reference frame), while the former is related to the movements of the segments relative to the COM and one another. The total kinetic energy of such a multi-link system can therefore be described as the sum of:
a) the kinetic energy of the segments arising from their change of speed with respect to the overall COM (internal work done); and
b) the kinetic energy of the overall COM with respect to the environment (external work done).

External work is readily and easily measured using global positioning systems and/or accelerometers, for example, but measurement of internal work is less straightforward.

Figure 1:
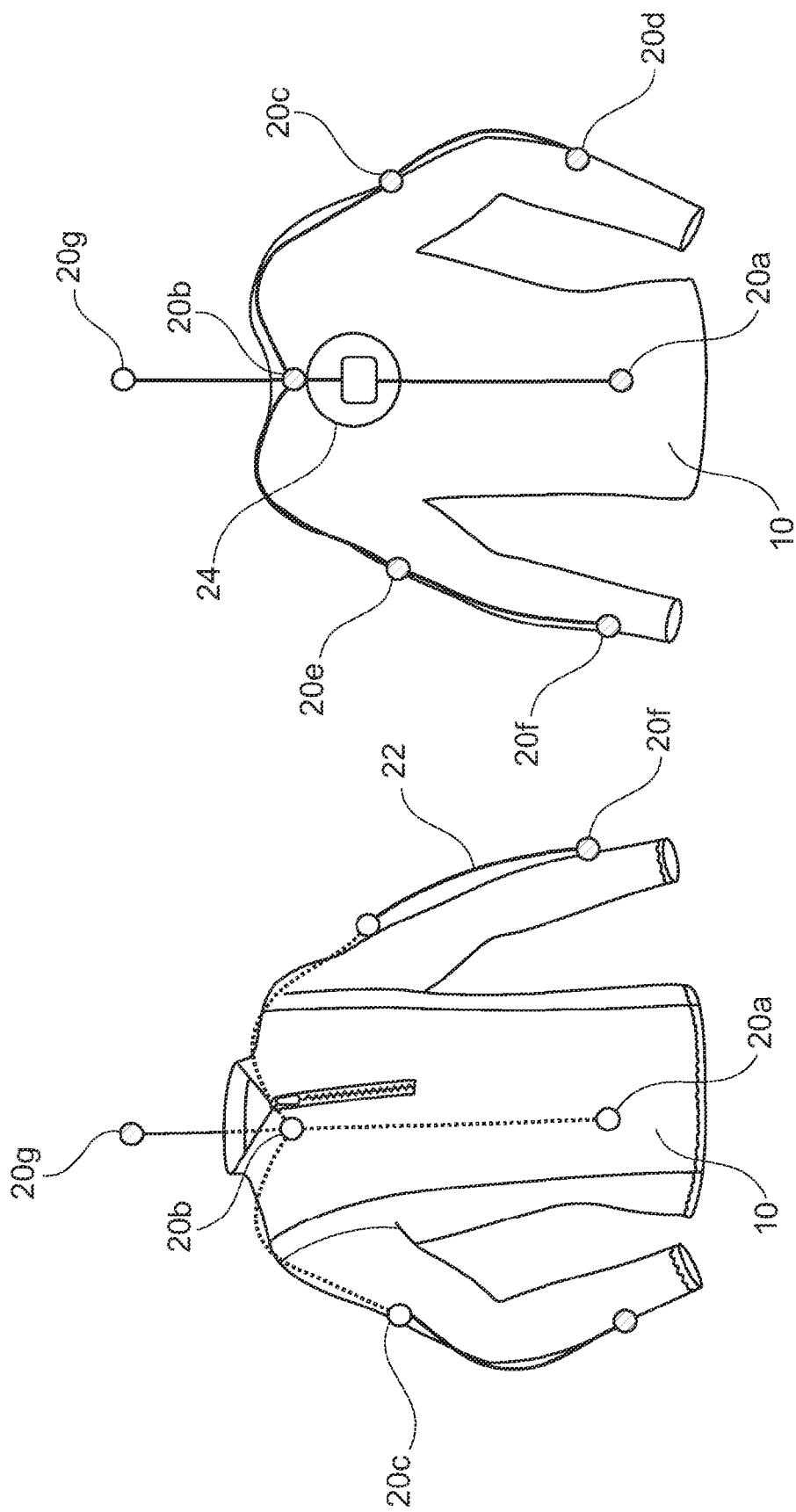
FIG. 1A is a front view of an item of clothing comprising a plurality of sensors in accordance with an embodiment of the present invention.
FIG. 1B is a rear view of the item of clothing of FIG. 1A.

FIGS. 1A and 1B show front and rear views of an item of clothing 10 for the upper body, which comprises a plurality of sensors 20a-g. Each sensor 20a-g may comprise one or more inertial measurement units (IMU) and/or a plurality of reference indicia, such as light emitters or reflectors that are measurable by an image capture device, such as a video camera. In a preferred embodiment, each sensor 20a-g comprises three IMUs, namely, a triaxial gyroscope, a triaxial accelerometer, and a triaxial magnetometer. Additionally, a GPS sensor (not shown) or one of the sensors 20a-g may be used to make global measurements of the COM of the entire body for calculation of external kinetic energy (global kinetic energy). Preferably then, one of the sensors is positioned close to the centre of mass of the moving body to obtain the global measurements. Since the COM will be inside the body, the sensor should be placed close to the COM location and preferably calibrated to more accurately reflect the position, orientation and/or movement of the COM.

In alternative embodiments, the sensors 20a-g may be on any base layer, rather than an item of clothing. In other embodiments, the sensors 20a-g may be adapted to be strapped onto a movable body individually and separately.

In the embodiment shown in FIGS. 1A and 1B, adjacent sensors 20a-g are connected by a cable 22 for data and electrical power transfer between the sensors 20a-g. In preferred embodiments, the cable 22 is coiled and embedded in the fabric of the item of clothing 10 or equivalent base layer.

Additionally, a base unit 24 is connected to the sensors 20a-g and houses a microcontroller for receiving measurement data from the sensors 20a-g and a transmitter, such as a Bluetooth or short distance RF transmitter, for transmitting measurement data (to a central control unit, for example).

In the preferable embodiment shown in FIGS. 1A and 1B, the sensors are arranged as follows:

| Sensor | Approximate Location |
|---|---|
| 20a | Spinous process of Lumber vertebrae |
| 20b | Spinous process of Thoracic vertebrae |
| 20c | Immediately below the deltoid tuberosity on upper right arm |
| 20d | Midway point between ulnar process and styloid process at distal end of lower arm |
| 20e | Immediately below the deltoid tuberosity on upper left arm |
| 20f | Midway point between ulnar process and styloid process at distal end of lower arm |
| 20g | On base of occipital bone (attached via a head band) |

Each sensor 20a-g is arranged to make measurements and produce a realtime three-dimensional 3×3 rotation matrix corresponding to the orientation of the corresponding segment (i.e. the sensor location). An example of such a 3×3 rotation matrix is given below.

|  | Column 1 | Column 2 | Column 3 |
|---|---|---|---|
| Row 1 | r11 | r12 | r13 |
| Row 2 | r21 | r22 | r23 |
| Row 3 | r31 | r32 | r33 |

Each segment therefore has a rotation matrix assigned to it and the sensor updates this matrix periodically (100 times per second, for example). With known (or closely approximated) segment lengths, it is possible to build up a kinetic chain of the body so that each segment or tracked body part has measured positional data in the global system in x, y and z dimension.

Figure 2:
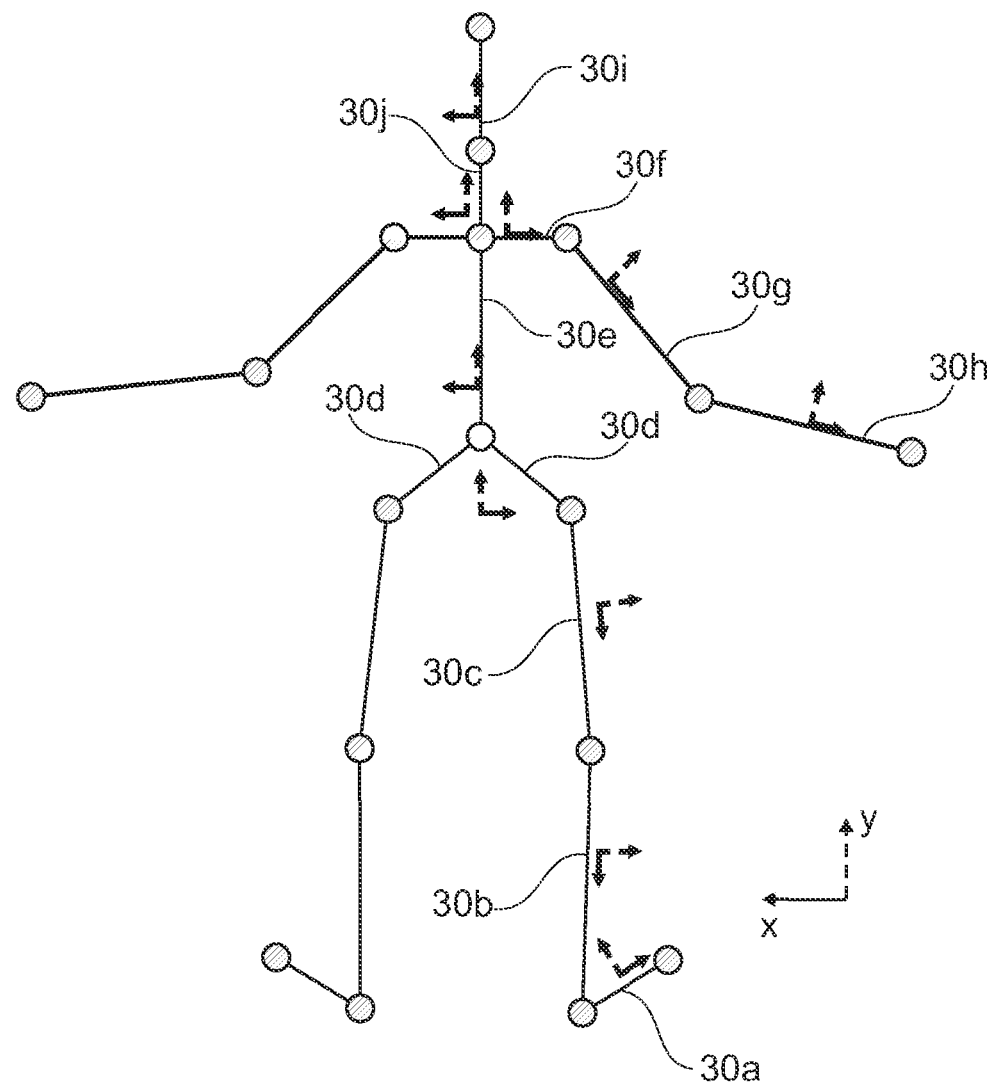
FIG. 2 is a schematic diagram showing a human body represented as a kinetic chain of movable segments.

FIG. 2 shows a human body represented as a schematic kinetic chain made up of segments. The segments shown in FIG. 2 are representative of body parts, as identified in the table below.

| Segment | Corresponding body part |
|---|---|
| 30a | Foot |
| 30b | Shank |
| 30c | Thigh |
| 30d | Pelvis |
| 30e | Lumbar and Thoracic Spine |
| 30f | Pectoral Girdle |
| 30g | Upper arm |
| 30h | Lower Arm and Hand |

-continued

| Segment | Corresponding body part |
|---|---|
| 30i | Head |
| 30j | Cervical Spine |

In this arrangement, column 1 of the rotation matrix for a given segment gives the global orientation of the long axis of the corresponding bone (indicated as x-axis in FIG. 2).

The above-described method of data acquisition relates to a kinematic analysis of motion of the moving body. In accordance with the present invention, the kinematic model is then supplemented with inertial characteristics, such as the relative masses and/or the mass moments of inertia of each segment. These characteristics may be obtained by direct analysis, or perhaps more conveniently, from data tables, such as published cadaver studies. Standard inverse dynamics calculations are then adopted to determine joint moments and forces, which in combination with the data from the kinematic model, will allow individual joint power output to be derived.

Inverse dynamics is the calculation of the (otherwise unknown) forces within a body based upon the (observable) kinematics of that body. It is based on Newton's laws of motion for a particle, applied to the motion of arbitrarily shaped bodies by Euler.

In the context of the present invention, each segment $30a\text{-}j$ represents a body part which is modeled as a rigid object, e.g. the forearm. Each link between adjacent segments $30a\text{-}j$ represents a mobile connection between the two segments $30a\text{-}j$, which is typically a joint, e.g. the elbow. Each segment $30a\text{-}j$ is modeled to have a fixed mass located as a point mass at its COM, and all joints are considered to be hinge (or ball and socket) joints. The moment of inertia of each segment $30a\text{-}j$ about its COM (or about either proximal or distal joints) is considered to be constant during the movement. Additionally, the length of each segment $30a\text{-}j$ is considered to remain constant during movement (i.e. the distance between hinge or ball and socket joints remains constant).

Each segment $30a\text{-}j$ has characteristics which influence its movement, but which do not change, namely, mass, location of the COM and the moment of inertia about the COM (i.e. its resistance to angular movement). These characteristics can be measured for individual subjects, but generic values are available in data tables which are based on more easily measurable quantities such as body mass and segment length. Each segment $30a\text{-}j$ also has observable dynamics characteristics, derivable from measurement at two or more of three points: the proximal joint, the distal joint, and the assumed COM. The dynamics characteristics for each point are: linear position, velocity and acceleration; orientation, attitude (rotation relative to some 'world' reference system), angular velocity (change in attitude with time) and angular acceleration (change in angular velocity with time). These characteristics need not be measured individually. For example, using motion capture one can accurately obtain proximal and distal joint positions at specific points in time, from which all linear and angular dynamic values can be calculated. Alternatively, using accelerometers and gyroscopes one can measure linear and angular acceleration (respectively), and thus estimate velocity and position3.

Using the measured dynamics characteristics for each segment and inverse dynamics, an estimate of the linear force and torque at the proximal joint can be calculated, provided that the linear force and torque at the corresponding distal joint is know. Since each proximal joint is also the distal joint of its parent segment, this means that, one can, in principle, recursively calculate the linear force and torque for each link in the model, provided that the linear force and torque is known for the end effectors. Newton's laws of motion for a particle, applied to the motion of arbitrarily shaped bodies by Euler, are the basis of inverse dynamics.

For a joint between a parent segment and a single child segment, the linear force and torque of the parent's distal joint are of equal magnitude to those of the child's proximal joint, but in the opposite direction, by virtue of Newton's third law of motion.

In accordance with the present invention, one or more pairs of the movable body parts are connected to one another with one or more resistive deformable elements, such as an elasticated band made, for example, from rubber. The resistive deformable elements add a resistance to relative movement of the connected body parts that increases the amount of energy required for relative movement. Thus, if the moving body is an exercising human, the exercise becomes more difficult and the human will inevitably expend more energy to make a movement compared with the same movement when no resistive deformable elements are present.

The present invention includes the energy required to deform the resistive deformable element(s) when the relevant body parts move relative to one another when calculating the relative expended energy. Therefore the calculated total expended energy incorporates the work done required to act against the resistive deformable elements.

In a particularly preferable embodiment, a human user wears a belt around their waist. The belt has two resistive deformable elements connecting the belt to two handles or straps for attachment to the user's hands or wrists. The user may then move their hands relative to their waist to act against the restoring elastic forces of the resistive deformable elements. With appropriately placed sensors, the work required to deform the resistive deformable elements can be included in the relative expended energy calculations of the hands moving relative to the waist. The calculation of work done in deforming the resistive deformable elements can be done using known properties of the resistive deformable elements, such as their dimensions, composition, spring constant and/or Young's modulus, for example.

An example of a suitable apparatus 1 incorporating resistive deformable elements is shown in FIG. 4A. The apparatus 1 comprises a belt 2 (or similar band) that is attachable around a user's waist or other part of the body, such as the chest. In the example shown in FIG. 4A, the belt 2 has a strap 4 that is attachable to a slot 5 by any suitable means for retaining the belt 2 around the user's waist. The strap 4, or the belt 2 more generally, may be adjustable so that the belt 2 can comfortably be used on waists of different sizes. Two resistive deformable elements 8,9 (e.g. elastic resistance bands) are each attached to the belt 2 at their first ends $8a,9a$ and are attached to handpieces 100 at their second ends $8b,9b$. The belt 2 may include a first sensor such as a global positioning system (GPS) sensor and/or an inertial measurement unit and/or a first plurality of reference indicia measurable by an image capture device, for measuring position data and/or orientation data and/or dynamic data of the user's trunk (which is approximate their center of mass). Similarly, the handpieces 100 may each include a sensor for measuring relative position data and/or orientation data and/or dynamic data of the hands that are holding the handpieces, relative to the user's trunk, as measured by the first sensor. The sensors on the handpieces may be an inertial measurement unit and/or a second plurality of reference indicia measurable by an image capture device.

Figure 4B:
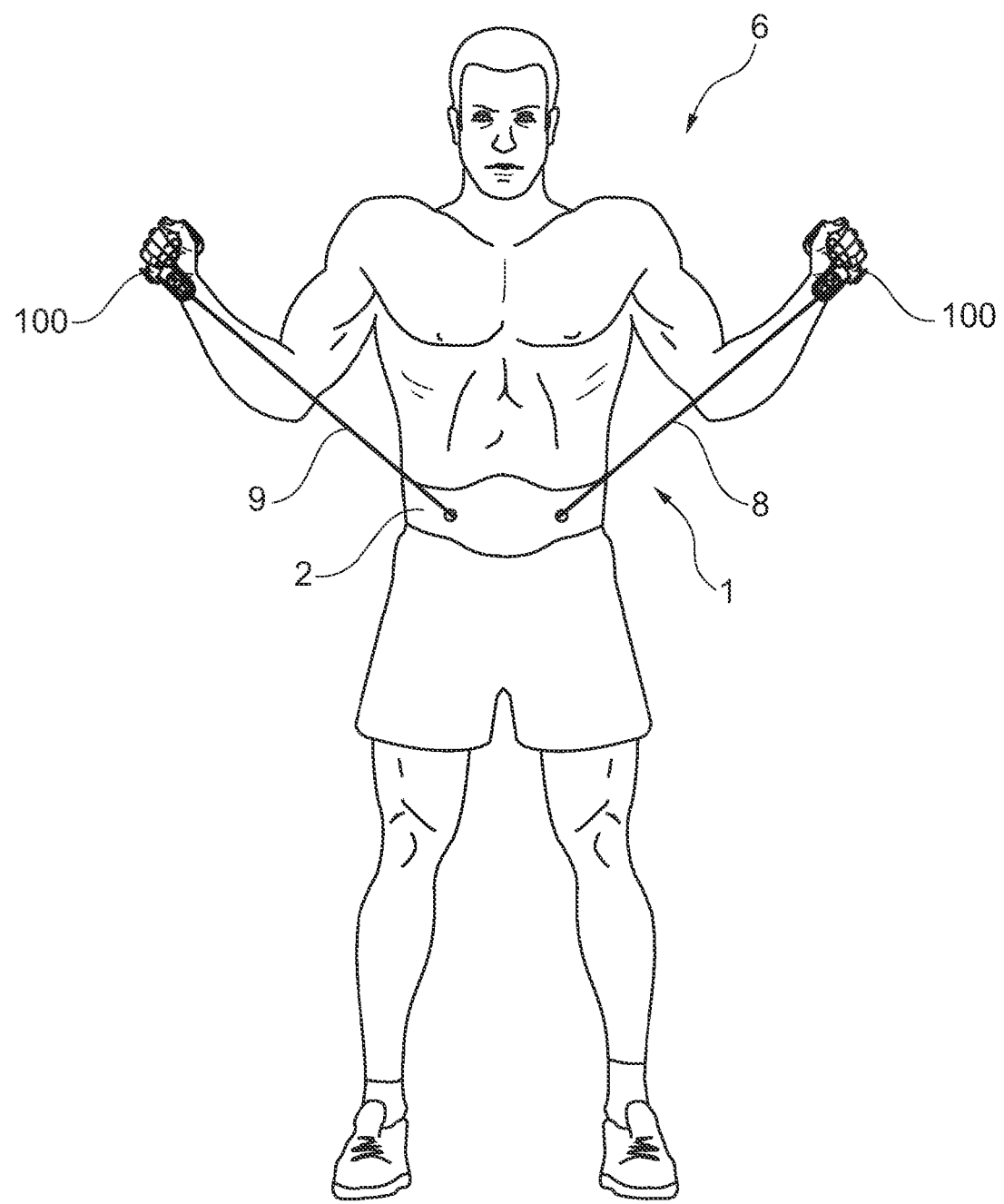
FIG. 4B shows a user wearing the apparatus shown in FIG. 4A.
Figure 5:
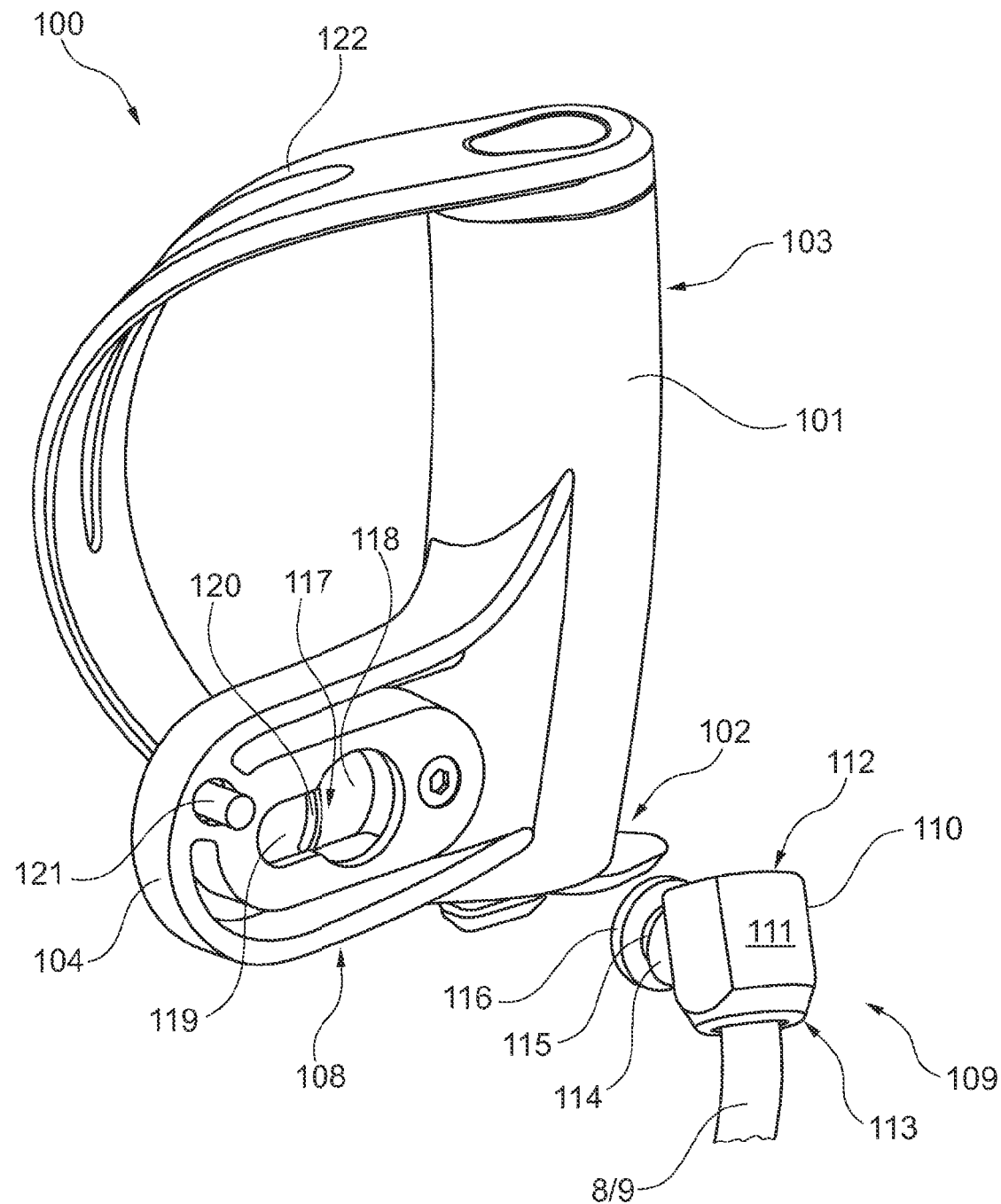
FIGS. 5 to 11 show various views of an embodiment of a handpiece for use as part of the apparatus shown in FIGS. 4A and 4B.
Figure 6:
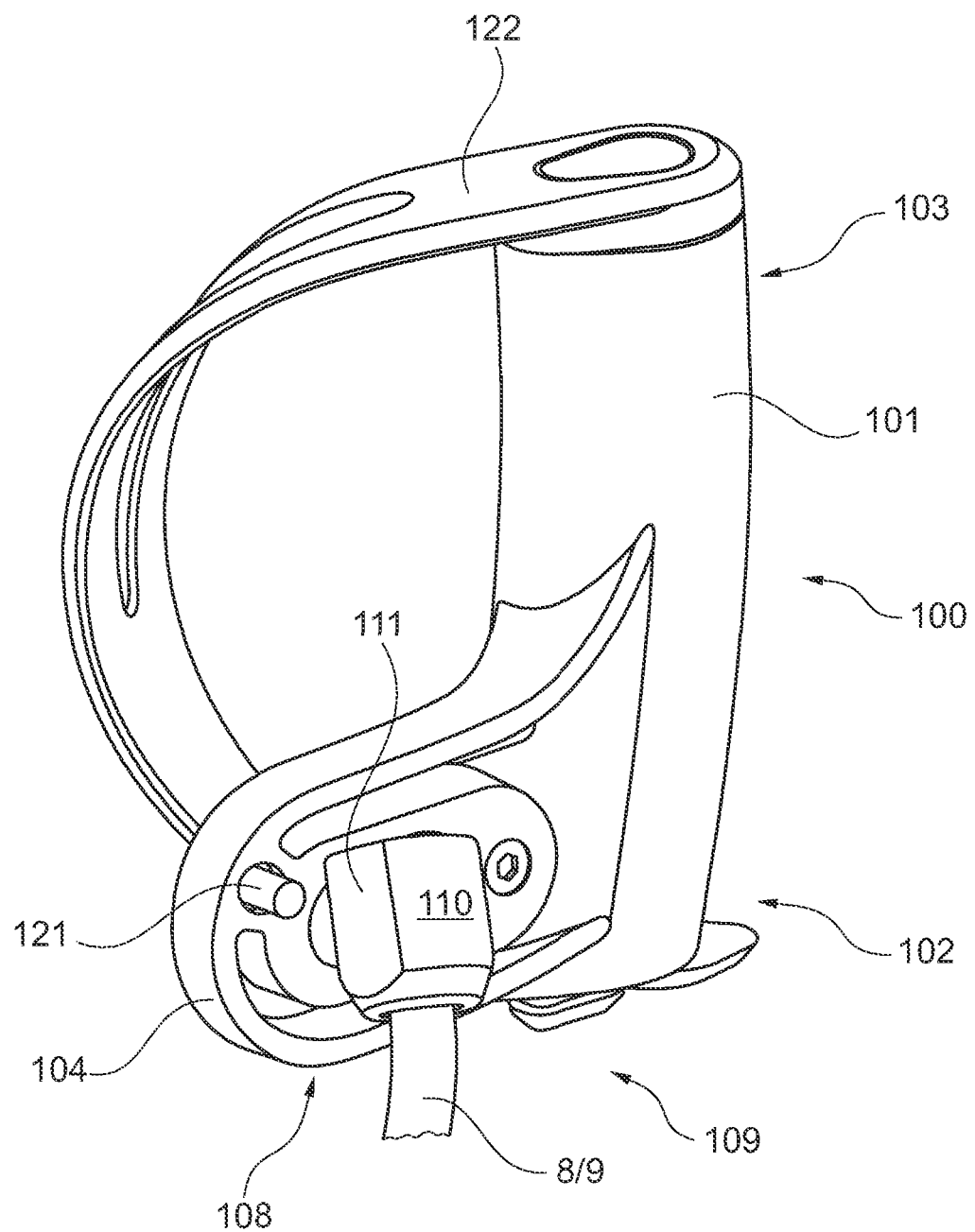

FIG. 4B shows a user 6 wearing the apparatus 1 shown in FIG. 4A. As the user 6 moves his/her hands whilst holding the handpieces 100, the resistive deformable elements 8,9 will deform (e.g. stretch) as the distance between the first ends 8a,9a and the second ends 8b,9b varies. Knowing the physical properties of the resistive deformable elements 8,9, the calculation of energy expenditure can include the energy required to deform the resistive deformable elements. Since the sensors on handpieces 100 will also provide information that will enable the direction of deformation (of the resistive deformable elements 8,9) to be determined, a more accurate calculation of the energy required to deform the resistive deformable elements 8,9 can be achieved for use in the overall calculation of energy expenditure. To illustrate this point, one must consider that different muscles will be used to extend (or otherwise deform) the resistive deformable elements 8,9 in different directions. Therefore, by measuring the extent of deformation and the direction and accounting for the physical properties of the resistive deformable elements 8,9, physiological considerations can provide an accurate calculation of energy expended by the user in achieving the deformation.

One or two handpieces 100 may be employed. Similar devices for attaching to other parts of the body (e.g. feet) may additionally or alternatively be employed, where the similar devices may be attached to the belt (or an additional band) by a resistive deformable element.

Referring to FIGS. 5 to 11, there is shown various views of a specific embodiment of the handpiece 100 of FIGS. 4A and 4B. FIGS. 5 to 11 show a lefthand handpiece 100 and it will be appreciated like configuration can be provided for a right handed handpiece 100.

Figure 10:
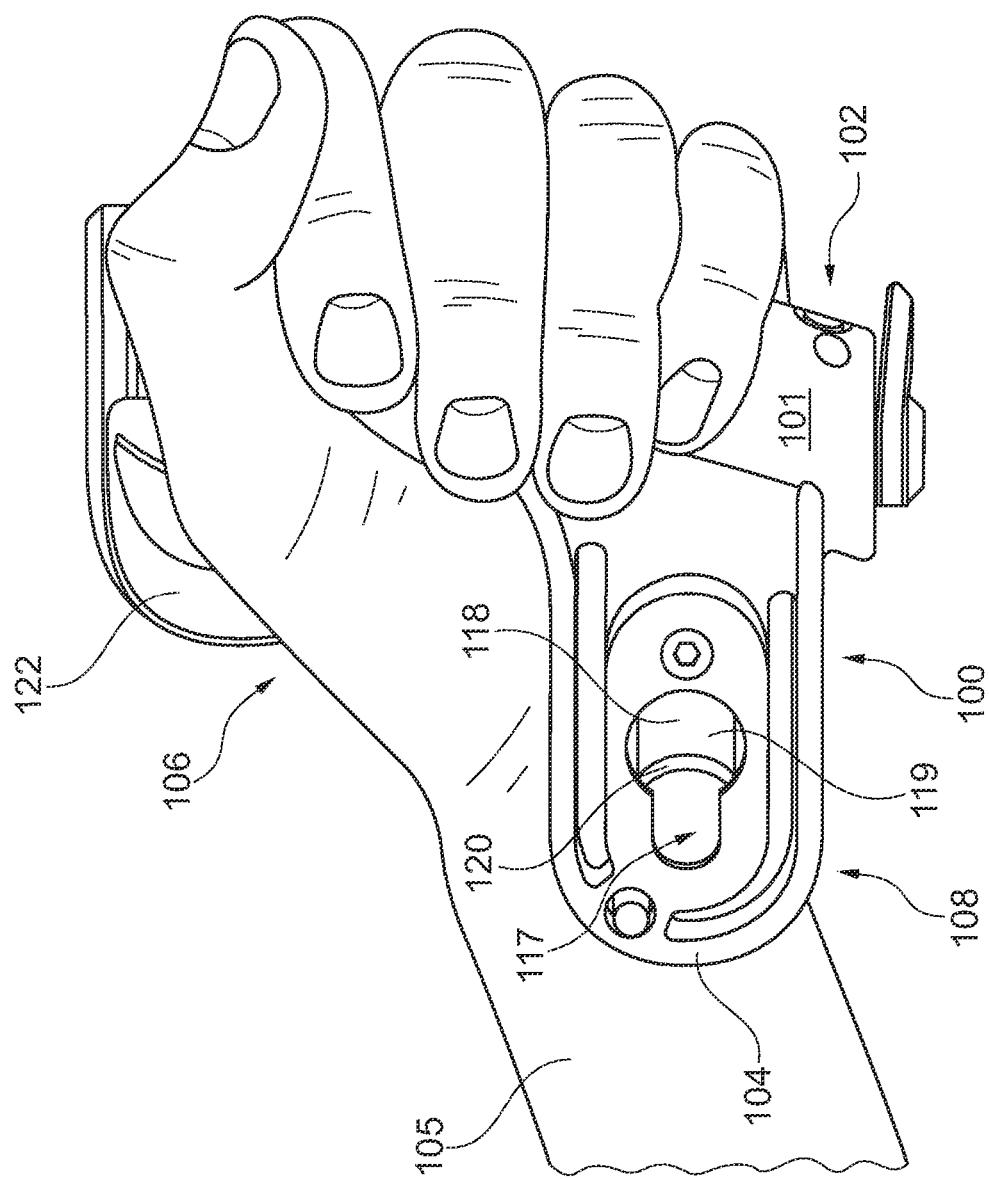

The handpiece 100 includes a handgrip 101 to be grasped by the person 19, the hand 106 of which is shown in FIG. 10. The handgrip 101 extends between a lower end 102 and a spaced apart upper end 103. The handgrip 101 is contoured to fit the profile of an attached hand for comfort of a person 19.

A wrist extension 104 is integrally formed with the handgrip 101 and extends from the lower end 102 of it. The wrist extension 104 is sized and shaped to abut the wrist 105 of the person 19 beyond their hand 106 to prevent or significantly oppose adduction or abduction, and extension or flexion, of the hand 106 when holding the handpiece 100. That is, the hand 106 and wrist 105 are maintained in a straight position with substantially no, or some fixed, adduction or abduction; extension or flexion. In other words, the hand is not moveable relative to the fixed position holding the handgrip 101. This is most advantageous for the reasons described below.

The wrist extension 104 has an inner facing portion (or inner face) 107 to be disposed against the base of the hand 106 and the wrist 105 and to support the region to prevent the flexion/extension and adduction/abduction movement. This significantly reduces wrist fatigue of the person 19 using the exercise device 1 with the handpieces 100. The wrist extension 104 has an outer facing portion (or outer face) 108 facing in a direction away from said wrist 105. The wrist extension of the preferred embodiment is substantially planar.

The outer face is adapted to releasibly receive one end 109 (best shown in FIG. 9) of a resistance band 8/9. The resistance band end 109 includes a resistance band connector 110 which is best shown in FIGS. 3, 5, 6, 9 & 11. The connector 110 has a body 111 extending between a top end 112 and a lower end 113 where the resistance band 8/9 attaches. The resistance band 8/9 is able to rotate about an axis parallel to said resistance band 8/9 but not move away from the lower end 113.

Figure 11:
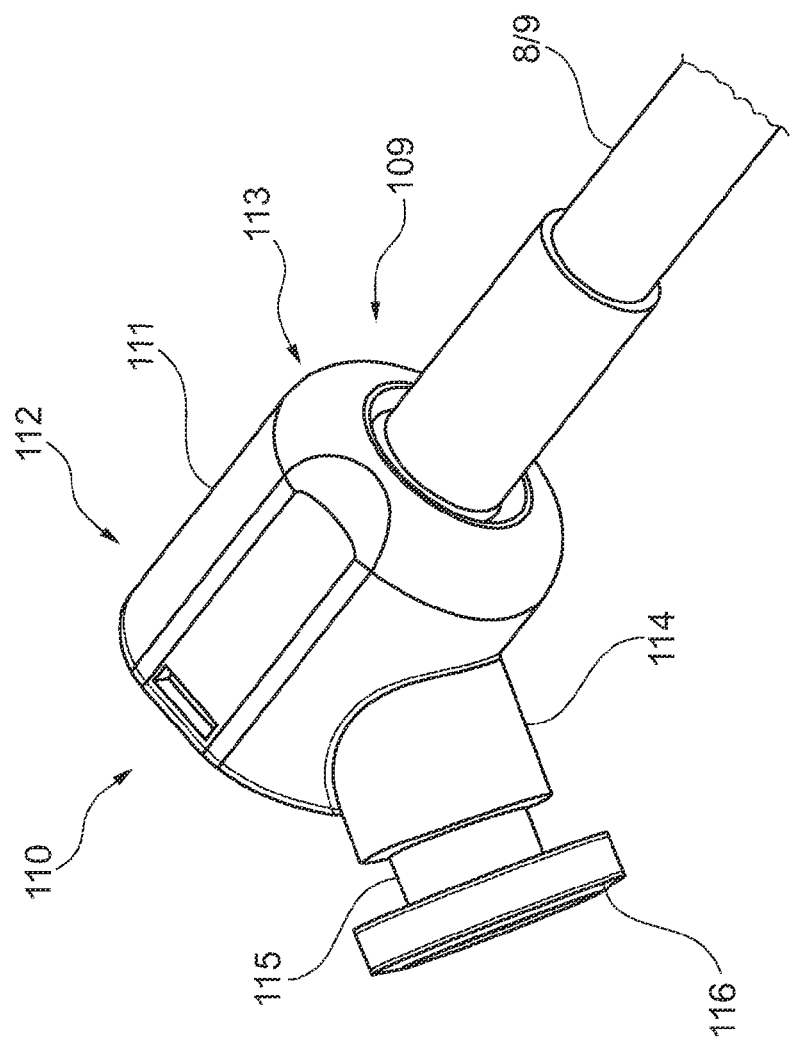

As best seen in FIG. 11, the connector 110 has a substantially cylindrical extension portion 114 mounted to the body 111 towards the top end 112. The extension portion 114 projects upwardly and outwardly. It can be seen in the preferred embodiment that the longitudinal axes of the body 110 and extension portion 114 are disposed at an angle less than 90° to each other. A connector head support shaft 115 extends from the extension portion 114. A connector head 116 is disposed on an end of the head support shaft 115 at an end distal the extension portion 114.

The wrist extension outer face 108 includes a shaped slot 117 configured to allow the head support shaft 115 to be retained thereby to able to slide therealong. One end of the slot 117 has an opening 118 to receive the connector head 116 and the remainder of the slot is smaller than the diameter of the connector head 116 to retain the connector head 116. A latch plate 119 is disposed behind the slot 117 and extends parallel to it. The latch plate 119 prevents movement of the connector head 116 too far past the slot 117 so that the head support shaft 115 is in the slot 117 so it is retained thereby except at the opening 118.

The latch plate 119 includes a pin 120 extending into the slot 117 and movable clear of it by pressing button 121. The latch plate 119 is resiliently biased to prevent movement of the head support shaft 115 therepast. This allows connection and disconnection of the connector 110 from the handpiece 100 and whilst retained in the slot 117, the connector extension portion 114 is able to rotate about an axis substantially perpendicular to a plane formed by the outer face 108. Advantageously, the resistance band 8/9 projects away from the wrist extension 104 when in use.

A strap 122 is mounted at each end to a respective lower 102 and upper 103 ends. The strap is releasibly attached at the lower end 102 and has an adjustable length. In the preferred embodiment shown, a knob projects from the lower end 102 to retain one of a plurality of apertures along the strap.

Figure 7:
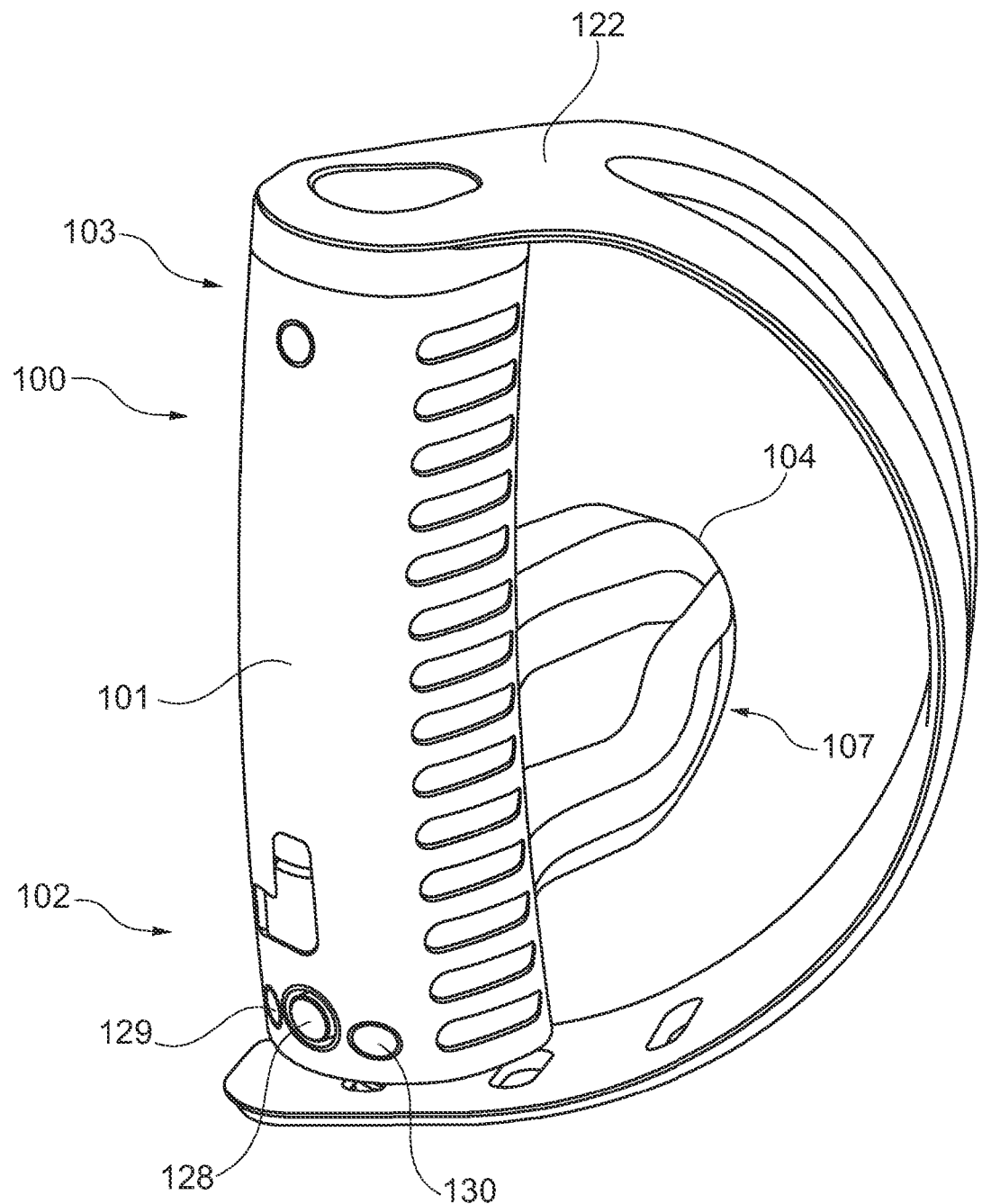
Figure 8:
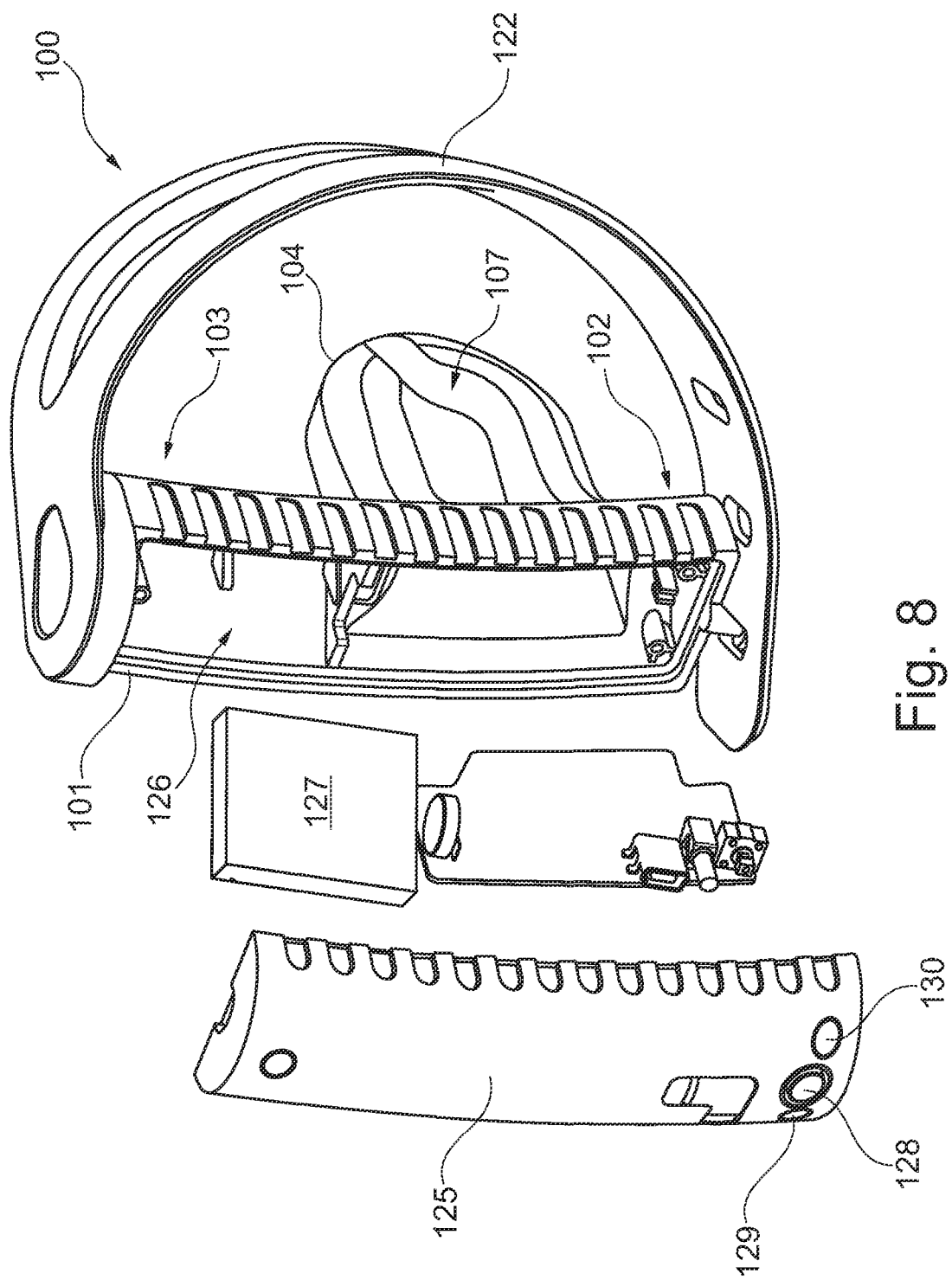
Figure 9:
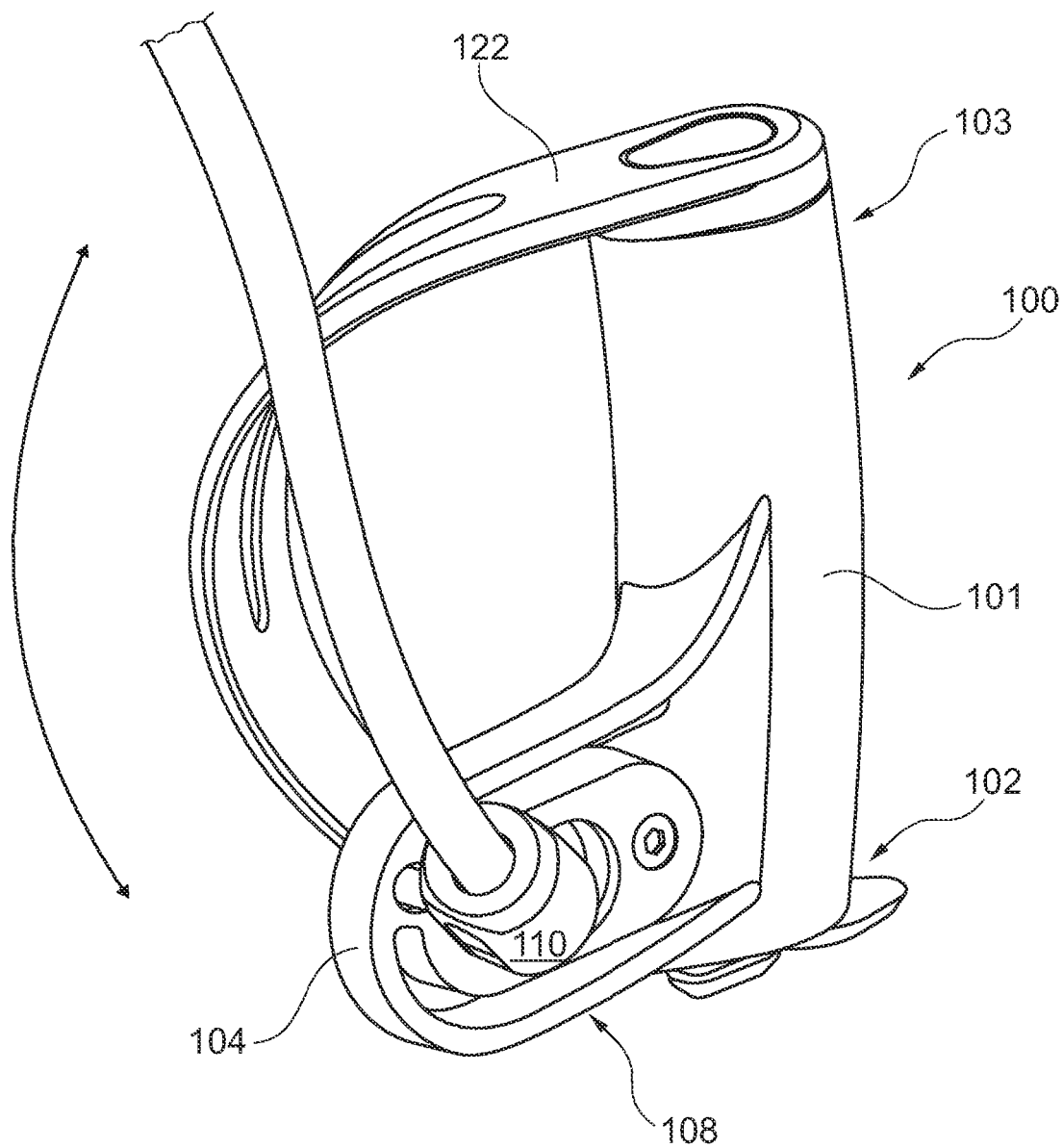

In addition to reducing wrist fatigue and allowing the connector 110 to swivel clear of the wrist extension 104, the handpiece 100 includes position sensing and transmission means. Referring particularly to FIGS. 7 and 8, a cover 125 forms part of the handgrip 101 covering a cavity 126. Within the cavity 126, a position sensor in the form of an accelerometer in the case of the preferred embodiment, is mounted to record movement of the handpiece 100 relative to a position receiver (not shown) disposed in the belt 2.

Signals from the position sensor are sent to the position receiver wirelessly and a battery (not shown) and an accelerometer control circuit and processor 127 (shown integrated) configured to receive the accelerometer signals and transmit those to the position receiver in the belt. A power button 128, USB connector port 129 for programming or data retrieval (from associated memory in the handpiece 100) and a calibration button 130 are provided. The calibration button 130 is depressed when the resistance band 8/9 are in a relaxed state or fully stretch so that a base point is determined for movement signals provided by the accelerometer.

In this way, movement of the accelerometer position sensor corresponds to the length of stretching of the resistance bands 8/9. Any preferred wireless handpiece positioning means as desired because the hand piece allows energy expended without the typical not insignificant energy expenditure in the flexion/extension or adduction/abduction of the wrist which is substantially eliminated. The person 19 thus more accurately calculates their energy expenditure of the intended anatomical regions or muscle groups from exercising with the device 1 in stretching the resistance bands 8/9.

The position receiver may have a controller associated therewith to transmit the accelerometer signals to a remote computing device for that device to process and calculate energy expenditure. Alternatively, the position receiver may compute the movement and associated energy expenditure of the accelerometer position sensor and send this data to the remote computing device. The accelerometer controller may also have associate memory to retain sensed data for transfer via the USB port 129.

In place of the accelerometer may be any inertial measurement unit that includes any one or more of an accelerometer, gyroscope, magnetometer and/or ultrasound receiver. Additionally or alternatively, a plurality of reference indicia measurable by an image capture device may be used in place or in addition to the inertial measurement unit.

Although the use of inverse dynamics in the context of the present invention yields good results in terms of the accuracy of energy expenditure, there are, nevertheless, inherent limitations associated with the technique as described below. In accordance with a preferable embodiment of the invention, the additional application of forward dynamics acts to mitigate these inherent limitations and is discussed in more detail below.

In a study to demonstrate the accuracy of the present invention, the calculated expended mechanical energy was compared with collected indirect calorimetry data. Verification data was collected using a Polar® heart rate monitor, a portable indirect calorimetry device (attached by a chest harness) with a flexible face mask (Cosmed K4b2). Simultaneously, in accordance with the present invention, motion measurement sensors were placed on anatomical landmarks on the upper body, belt and hand grips. The participant then played a computerized boxing game using the motion measurement sensors to control the game, prompting periods of high-intensity exercises followed by periods of rest. The participant also had resistance bands of randomly allocated elasticity (low, medium and high) connected between various body parts (e.g. hand and waist) requiring the participant to act against the resistance of the bands during movement. The bands were interchanged between sessions such that the participant used each band once. Following each session, the participant was allowed sufficient rest before repeating the session with another resistance band of different resistance. The overall time taken for the high-intensity interval training was approximately 20 mins. The calorific values were recorded using indicted calorimeter and inverse dynamics calculations were performed as described above.

The proportion of work done (total expended energy), as measured by the present invention, for all time frames, for all subjects, is given in the table below, for each joint/body part studied.

| | Proportion of work done (%) | |
| --- | --- | --- |
| Joint/body part | Low-stiffness band | High-stiffness band |
| Left elbow | 10.30 | 10.07 |
| Right elbow | 9.90 | 11.89 |
| Left shoulder | 14.11 | 16.32 |
| Right shoulder | 17.32 | 20.14 |
| Left pectoral girdle | 4.00 | 4.50 |
| Right pectoral girdle | 5.22 | 7.67 |
| Trunk | 39.16 | 29.40 |

The results compare closely with a study by Rogers et al. (2003), who used motion capture to estimate the power in the wrist, elbow and shoulder joints of adult subjects powering wheelchairs. During the Rogers et al. (2003) study, it was found that the average rotational joint power in the shoulder was 56% higher than the combined rotational joint power of the wrist and elbow. In the present study, over the course of 30 high-intensity interval training session, the shoulder power (left shoulder and right shoulder) exceeded the elbow power (left elbow and right elbow) by 56%, 45% and 61% for the low, medium, and high strength resistance bands, respectively. The largest proportion of energy at any joint was found to be the torso root (trunk). This is due to the large mass of the torso, as well as the fact that linear force is taken into account here, which represents the work done by the lower body in moving the torso. The low-stiffness band appears to illicit greater mechanical work in the proximal segments such as in the core muscles (trunk), whereas the high-stiffness band appears to generate a greater proportion of the power from the distal segments.

Figure 3:
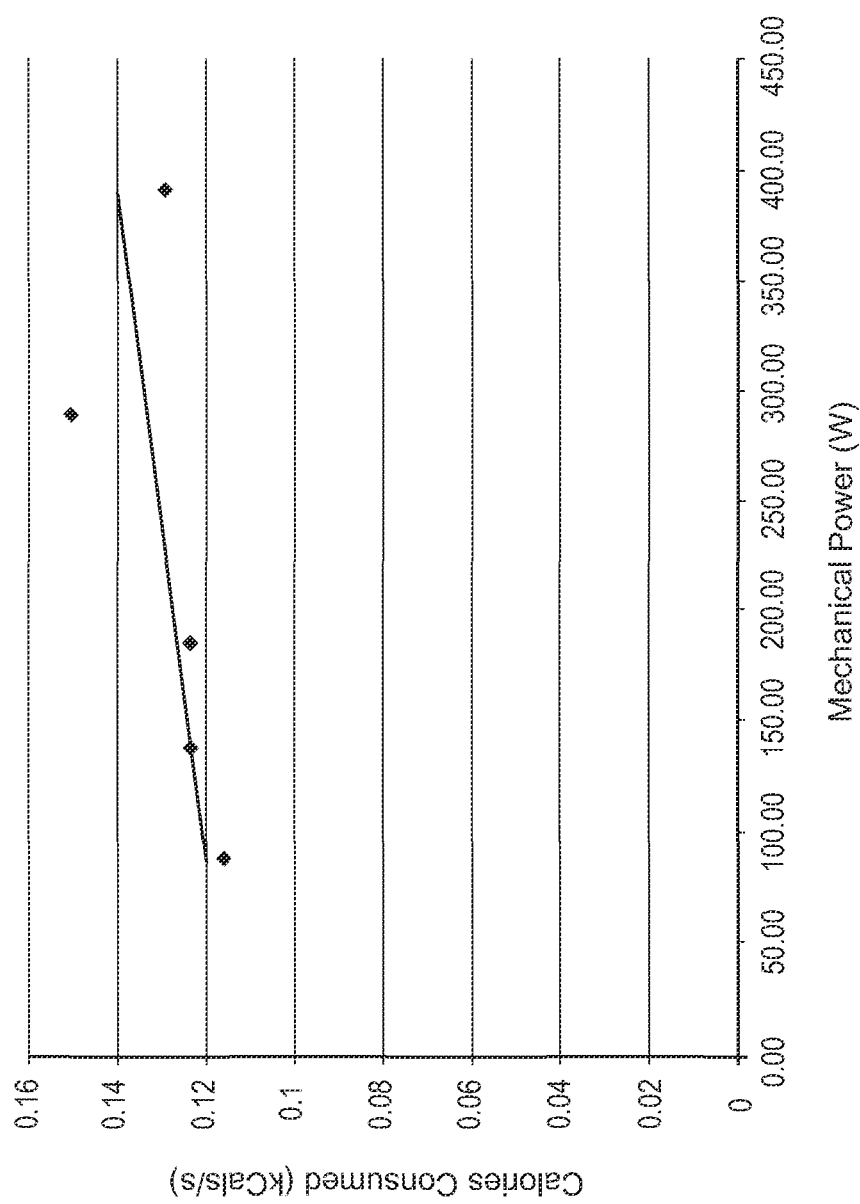
FIG. 3 is a graph comparing mechanical power output of the upper body derived using inverse dynamics in accordance with the present invention and calories consumed (derived using indirect calorimetry) during repeated high-intensity interval training in a boxing activity.

As shown in FIG. 3, there is a notable correlation between the mechanical power output, as calculated using the present invention, and the calories consumed, derived from indirect calorimetry (correlation coefficient, R=0.6) indicating that the summed mechanical power is related to the calories consumed. There are several reasons why a stronger correlation was not obtained. Firstly, indirect calorimetry as used here measures the respiratory ratio between oxygen consumed and $CO_2$ expired and hence does not include calories consumed due to anaerobic processes. These brief high-intensity exercise periods will include a substantial anaerobic load on the muscles and thus the measures of calories consumed will be lower than the actual calories consumed. There are also limitations of the inverse dynamics technique for deriving mechanical energy expended. These are:

1. The inverse dynamics approach only measures net joint power and cannot be used to differentiate between positive and negative powers. Co-contraction of muscles providing positive and negative power in the muscles are not represented in the model (but are inevitable in all human movements); and 2. The inverse dynamics method does not include representation of elastic energy storage and return. It has been found that structures such as the Achilles' tendon can account for over 50% of the joint power but only 18% of the total net metabolic power.

Taken together these limitations will lead to an overall underestimate of the muscle work done. However, many of the limitations of the inverse dynamics approach can be overcome with additional use of forward dynamics. The use of forward dynamics enables the calculation of expended energy to consider input joint and tissue loading, muscle fiber and/or tendon force and power, and elastic energy storage and return in tendons. These parameters can be combined to simulate and predict external (and measureable) variables such as joint kinematics or kinetics. These simulations provide both a consistent mechanical solution that can be interrogated at multiple levels (muscle fiber, musculotendon, net joint moment and whole body work). Such simulations are particularly powerful because they allow for the identification of causal relationships between the neural control inputs, muscle force and power output, and the task performance.

Forward dynamics itself also has inherent limitations. In particular, many of the quantities being investigated cannot be measured (hence the importance of simulations). Modeling requires assumptions regarding anatomy, muscle physiology and structural and mechanical properties including the interaction between the model and the ground. However, if quantities such as muscle work are of interest, confidence in the results can be gained when:

Each muscle is excited at the appropriate point in the gait cycle,

The overall mechanics of the movement are sufficiently similar to the measurable observations, Energy/momentum balances are assured.

Comparisons with experimental observations such as joint powers based on inverse dynamics-based quantities can be used to confirm that the overall kinetics of the movement are sufficiently similar to the experimental observations. Similarly, comparisons with joint movements can be used to confirm that the overall kinematics of the movement are correct. Thus by measuring the joint kinetics and kinematics, a mechanism is provided to internally validate forward dynamic simulations, and open up new approaches to the quantification of muscle energetics during free-living activity.

Whilst the skilled reader will appreciate that variations of the present invention are possible within the scope of the claims, the present invention requires the measurement of position, orientation and/or other dynamic quantities of a first body part to create global data which may be used to calculate external expended energy of the moving body. Additionally, measurements of the position, orientation and/or other dynamic quantities of a second (and any subsequent) body part may be taken and used to calculate the relative expended energy of those parts of the body, relative to the first part. The sum of these energies provides the total expended energy of the body. Considering the human body, the above described inverse dynamics model may be used to improve the accuracy of calculation of energy expended by moving limbs using the measured data and known or derivable data of limbs and body parts (such as relative masses and mass moments of inertia). In a further improvement, the total energy expenditure calculation may be done using a forward dynamics simulation which quantifies the effect of internal gait parameters on external biomechanical variables. In particular, a forward dynamics simulation could be run simultaneously with a measurement system that implements inverse dynamics. The calculated energy values from the inverse dynamics model may then be used to iteratively check the validity of the simultaneous forward dynamics simulation, where discrepancies between the measured inverse dynamics and the forward dynamics with respect to joint kinematics and power would be fed back into the forward dynamics model to improve its accuracy. An additional benefit of utilizing a forward dynamics simulation in the present invention is that individual muscle data is provided which may be used to assess the specific effectiveness of an exercise or activity. This may be significantly valuable in quantifying and monitoring the effect of exercise on physiological conditions such as T2D.

Both internal and external work are the combination of kinetic and potential energy. More simply, the work done is not only related to accelerations but also the distance travelled by that object. Thus, the accuracy of both calculated internal and external work done will depend largely on the quality of the positional information captured during the session. The present invention provides an accurate and convenient method and apparatus for measuring total expended energy which may be used to monitor a human subject during exercise or free living. Thus, the present invention allows the specific effectiveness of particular activities may be monitored in relation to health or physical training which calorie-based energy monitors are unable to do accurately. The present invention is particularly suited to monitoring the expended energy of a person during free living, which lab-based techniques are unable to do.

The present invention may be used as part of a computer-based game whereby the user's activity, as monitored by the above-described method and apparatus of the present invention, controls the game. In particular, the user's success in the game may depend on the user expending a predetermined amount of energy. Such a game could only be played correctly when the user was partaking in exercise of a particular intensity level, and thereby form part of a serious exercise regime. This is in contrast to many accelerometer based interactive games where the system can be "tricked" into Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

American Diabetes Association: Standards of medical care in diabetes—2008. Diabetes Care 2008, 31(Suppl 1):S12-54.

David Andre and Donna L. Wolf. Recent Advances in Free-Living Physical Activity Monitoring: A Review. J Diabetes Sci Technol. 2007 September; 1(5): 760-767.

Asp S, Daugaard J R, Kristiansen S, et al. Eccentric exercise decreases maximal insulin action in humans: muscle and systemic effects. J Physiol. 1996; 494:891-898.

Babraj, J. A., Vollaard, N. B J., Keast, C., Guppy, F. M., Cottrell, G., Timmons, J. A. (2009). Extremely short duration high intensity interval training substantially improves insulin action in young healthy males. BMC Endocrine Disorders, 9(3), 1-8.

Dunstan D W, Daly R M, Owen N, Jolley D, de Courten M, Shaw J, Zimett P: High-intensity resistance training improves glycemic control in older patients with type 2 diabetes. Diabetes Care 25: 1729-1736, 2002 Castaneda et al (2002)

Dumas, R., Aissaoui, R. and De Guise, J. A. (2004). A 3D generic inverse dynamic method using wrench notation and quaternion algebra. Computer Methods in Biomechanics and Biomedical Engineering 7:3 pp 159-166.

Fenicchia L M, Kanaley J A, Azevedo J L Jr, et al. Influence of resistance exercise training on glucose control in women with type 2 diabetes. Metabolism. 2004; 53:284-289.

Godin G, Desharnais R, Valois P, Lepage P, Jobin J, Brader R: Differences in perceived barriers to exercise between high and low intenders: observations among different populations. Am J Health Promot 1994, 8:279-285.

Holten M K, Zacho M, Gaster M, Juel C, Wojtaszewski J F, Dela F: Strength training increases insulin-mediated glucose uptake, GLUT4 content, and insulin signalling in skeletal muscle in patients with type 2 diabetes. Diabetes 53:294-305, 2004.

Howlett K, Mathews A, Garnham A, Sakamoto K. The effect of exercise and insulin on AS160 phosphorylation and 14-3-3 binding capacity in human skeletal muscle. Am J Physiol Endocrinol Metab. 2007; 294:E401-E407.

Ivy J L: Exercise physiology and adaptations to training. In Handbook of Exercise in Diabetes. 2nd ed. Ruderman N, Devlin J T, Schneider S H, Kriska A, Eds. Alexandria, Va., American Diabetes Association, 2002, p. 23-62.

Koopman R, Manders R J, Zorenc A H, et al. A single session of resistance exercise enhances insulin sensitivity for at least 24 h in healthy men. Eur J Appl Physiol. 2005; 94:180-187.

Kirwan J P, Hickner R C, Yarasheski K E, et al. Eccentric exercise induces transient insulin resistance in healthy individuals. J Appl Physiol. 1992; 72:2197-2202.

Lakka T A, Laaksonen D E: Physical activity in prevention and treatment of the metabolic syndrome. Appl Physiol Nutr Metab 2007, 32(1):76-88.

Lund S, Holman G D, Schmitz O, Pedersen O: Contraction stimulates translocation of glucose transporter GLUT4 in skeletal muscle through a mechanism distinct from that of insulin. Proc Natl Acad Sci USA 92:5817-5821, 1995.

Richter E A: Glucose utilization. In Handbook of Physiology. Rowell L B, Shepherd J T, Eds. New York, Oxford University Press, 1996, p. 912-951.

Rogers, M. M., McQuade, K. J., Rasch, E. K., Keyser, R. E., Finley, M. A. (2003) Upper-limb fatigue-related joint power shifts in experienced wheelchair users and non-wheelchair users. Journal of Rehabilitation Research and Development 40(1): 27-38.

Sigel, R. J., Kenny, G. P., Wasserman, D. H., Castaneda-Scepa, C. (2004). Physical Activity/Exercise and Type 2 Diabetes. Diabetes Care, 27(10), 2518-2539.

Turcotte, L. P., Fisher, J. S. (2008). Skeletal Muscle Insulin Resistance Roles of Fatty Acid Metabolism and Exercise. Physical Therapy, 88(11), 1279-1296.

Venables M C, Shaw C S, Jeukendrup A E, Wagenmakers A J. Effect of acute exercise on glucose tolerance following postexercise feeding. Eur J Appl Physiol. 2007; 100:711-717.

Winter, D. A. (2005). Biomechanics and motor control of human movement, 3rd edition. Hoboken N.J., Wiley.

The invention claimed is:

1. A method of measuring expended energy of a moving body, comprising the steps:
   i) providing at least one first sensor for measuring position data and/or orientation data and/or dynamic data of a first part of the moving body;
   ii) providing at least one second sensor for measuring relative position data and/or orientation data and/or dynamic data of a second part of the moving body, wherein the second part is moveable relative to the first part and connected to the first part by a first resistive deformable element that is external to the moving body;
   iii) using the at least one first sensor to obtain first measurement data indicative of the position and/or orientation and/or dynamics of the first part over a period of time and subsequently transferring the first measurement data to a receiver and transforming the first measurement data obtained from the at least one first sensor by the receiver into a global expended energy of the first part relative to a reference frame;
   iv) using the at least one second sensor to obtain second measurement data indicative of the position and/or orientation and/or dynamics of the second part over said period of time and subsequently transferring the second measurement data to the receiver and transforming the first measurement data and the second measurement data by the receiver into a relative expended energy of the second part relative to the first part, wherein the transformation into relative expended energy includes transformation by the receiver of data indicative of the energy required to deform the first resistive deformable element when moving the second part relative to the first part; and
   (v) calculating by the receiver the total expended energy of the moving body by summing the global expended energy with the relative expended energy;
   wherein the at least one first sensor comprises a global positioning system (GPS) sensor and/or an inertial measurement unit and/or a first plurality of reference indicia measurable by an image capture device; and
   the at least one second sensor comprises an inertial measurement unit and/or a second plurality of reference indicia measurable by an image capture device;
   vi) providing at least one nth sensor for measuring relative position data and/or orientation data and/or dynamic data of an nth part of the moving body, wherein the nth part is moveable relative to an ith part, where n>2 and i<n;
   vii) using the at least one nth sensor to obtain nth measurement data indicative of the position and/or orientation and/or dynamics of the nth part over said period of time and subsequently transferring the nth measurement data to the receiver and transforming the nth measurement data and ith measurement data by the receiver into a relative expended energy of the nth part relative to the ith part; and
   wherein the step of calculating by the receiver the total expended energy of the moving body comprises summing the global expended energy with all relative expended energies for each nth and ith part.

2. A method according to claim 1, wherein the nth part is connected to an ith part by an nth resistive deformable element that is external to the moving body.

3. A method according to claim 1, wherein each at least one second sensor, and any nth sensor present, is arranged to produce a three-dimensional rotation matrix for each of the second and any nth part.

4. A method according to claim 3, wherein each three-dimensional rotation matrix is updated by the respective sensor periodically.

5. A method according to claim 4, wherein each three-dimensional rotation matrix is updated by the respective sensor 100 times per second.

6. A method according to claim 1, wherein the at least one first sensor is positioned close to the centre of mass of the moving body.

7. A method according to claim 1, wherein the moving body is a human body.

8. A method according to claim 7, wherein step (i) comprises disposing the at least one first sensor on or adjacent a first part of the moving body for measuring position data and/or orientation data and/or dynamic data thereof, and step (ii) comprises disposing the at least one second sensor in a handgrip device held by the hand of the moving body for measuring relative position data and/or orientation data and/or dynamic data thereof, wherein the handgrip device is moveable relative to the first part and connected thereto by the first resistive deformable element.

9. A method according to claim 8, wherein the at least one first sensor is attached to a band that is wearable by a user, and the handgrip device is connected to the band by the first resistive deformable element.

10. A method according to claim 9, wherein the relative expended energy of the second part relative to the first part and/or the nth part relative to the ith part is determined using inertial characteristic data associated with the second and the nth part, where the inertial characteristic data includes relative masses of the respective body parts and/or mass moments of inertia of each respective body part.

11. A method according to claim 10, wherein the inertial characteristic data is obtained, at least partly, from a data table.

12. A method according to claim 10, further comprising the step of running a forward dynamics simulation of the moving body to produce a second calculation of total expended energy, and iteratively improving the simulation using the first calculation of total expended energy.

13. A method according to claim 1, wherein the transformation into global or relative energy uses the integral of a power-time measurement obtained from said first, second and nth measurement data.

14. A method according to claim 1, wherein the first resistive deformable element and any nth resistive deformable element is an elasticated band.

15. An apparatus for measuring expended energy of a moving body, comprising:
- at least one first sensor for measuring position data and/or orientation data and/or dynamic data of a first part of the moving body;
- at least one second sensor for measuring relative position data and/or orientation data and/or dynamic data of a second part of the moving body, wherein the second part is moveable relative to the first part;
- a first resistive deformable element that is external to the moving body for connecting the second part to the first part, wherein the first resistive deformable element is arranged to deform and act to resist deformation when the second part is moved relative to the first part; and
- a control unit communicably coupled to the at least one first and second sensors to receive measurement data therefrom;
- wherein the at least one first sensor is arranged to make a first measurement of the position and/or orientation and/or dynamics of the first part over a period of time and transmit the first measurement data to the control unit;
- the at least one second sensor is arranged to make a second measurement of the position and/or orientation and/or dynamics of the second part over said period of time and transmit the second measurement data to the control unit; and
- the control unit is arranged to calculate a global expended energy of the first part relative to a reference frame from the first measurement, calculate a relative expended energy of the second part relative to the first part from the first and second measurements, wherein the calculation of relative expended energy includes the energy required to deform the first resistive deformable element when moving the second part relative to the first part, and calculate the total expended energy of the moving body by summing the global expended energy with the relative expended energy;
- wherein the at least one first sensor comprises a global positioning system (GPS) sensor and/or an inertial measurement unit and/or a first plurality of reference indicia measurable by an image capture device; and
- the at least one second sensor comprises an inertial measurement unit and/or a second plurality of reference indicia measurable by an image capture device;
- the apparatus further comprising at least one nth sensor communicably coupled to the control unit for measuring relative position data and/or orientation data and/or dynamic data of an nth part of the moving body, wherein the nth part is moveable relative to an ith part, where n>2 and i<n;
- wherein the at least one nth sensor is arranged to make an nth measurement of the position and/or orientation and/or dynamics of the nth part over said period of time and transmit the nth measurement to the control unit subsequently calculating a relative expended energy of the nth part relative to the ith part from the ith and nth measurements; and
- wherein the step of calculating the total expended energy of the moving body comprises summing the global expended energy with all calculated relative expended energies for each nth and ith part.

16. An apparatus according to claim 15, further comprising an nth resistive deformable element that is external to the moving body for connecting the nth part to an ith part, wherein the nth resistive deformable element is arranged to deform and act to resist deformation when the nth part is moved relative to the ith part.

17. An apparatus according to claim 15, wherein the sensors are arranged on, or form part of, an item of clothing, and the moving body comprises the wearer of the item of clothing.

18. An apparatus according to claim 17, wherein the sensors are arranged on the item of clothing such that, when worn, the at least one first sensor is arranged to measure position data and/or orientation data and/or dynamic data of the Lumber vertebrae of the wearer, and the at least one second sensor is arranged to measure position data and/or orientation data and/or dynamic data of the Thoracic vertebrae of the wearer.

19. An apparatus according to claim 15, wherein each sensor is connected to at least one other sensor by a cable, wherein the cable is arranged to carry electrical power to the sensors and/or allow the transfer of data between the sensors.

20. An apparatus according to claim 15, further comprising a transmitter communicably coupled to the sensors, wherein measurement data is transmittable to the control unit via the transmitter.

21. An apparatus according to claim 15, wherein the at least one second sensor is on a handgrip device to be held in the hand of a user for measuring relative position data and/or orientation data and/or dynamic data of the hand.

22. An apparatus according to claim 21, wherein the at least one first sensor is attached to a band that is wearable by a user, and the handgrip device is connected to the band by the first resistive deformable element.

23. An exercise system comprising:
an apparatus according to claim 15;
a computer system loaded with a game and in communication with the apparatus; and
a display unit communicably coupled to the computer system for displaying the game;
wherein the measurements made by the sensors are used by the computer to control the game, and the calculated total expended energy of the moving body is used as part of the game.

24. An exercise system according to claim 23, wherein the game comprises several stages that are completed upon the total expended energy exceeding a predetermined threshold.

* * * * *